US010465196B2

(12) United States Patent
Disney

(10) Patent No.: US 10,465,196 B2
(45) Date of Patent: Nov. 5, 2019

(54) TREATMENT OF C9FTD/ALS BY TARGETING RNA EXPANDED REPEAT SEQUENCES

(71) Applicant: THE SCRIPPS RESEARCH INSTITUTE, La Jolla, CA (US)

(72) Inventor: Matthew D. Disney, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/969,374

(22) Filed: May 2, 2018

(65) Prior Publication Data

US 2018/0334678 A1 Nov. 22, 2018

Related U.S. Application Data

(63) Continuation of application No. 15/503,524, filed as application No. PCT/US2015/045021 on Aug. 13, 2015, now abandoned.

(Continued)

(51) Int. Cl.
*A61K 31/40* (2006.01)
*C12N 15/63* (2006.01)
(Continued)

(52) U.S. Cl.
CPC ............ *C12N 15/63* (2013.01); *A61K 31/404* (2013.01); *A61K 31/7105* (2013.01);
(Continued)

(58) Field of Classification Search
CPC . C07D 403/12; A61K 31/4045; A61K 31/404
(Continued)

(56) References Cited

U.S. PATENT DOCUMENTS

2004/0063645 A1* 4/2004 Botyanszki .......... C07D 207/34 548/492

FOREIGN PATENT DOCUMENTS

GB 2241950 A * 9/1991

OTHER PUBLICATIONS

PubChem CID 395006 (Year: 2005).*

* cited by examiner

*Primary Examiner* — Shengjun Wang
(74) *Attorney, Agent, or Firm* — Geoffrey K. Cooper; Thomas Fitting

(57) ABSTRACT

A repeat expansion in C9ORF72 causes frontotemporal dementia and amyotrophic lateral sclerosis (c9FTD/ALS). RNA of the expanded repeat ($r(GGGGCC)_{exp}$) forms nuclear foci or undergoes repeat-associated non-ATG (RAN) translation producing "c9RAN proteins". Since neutralizing $r(GGGGCC)_{exp}$ could inhibit these potentially toxic events, we sought to identify small molecule binders of $r(GGGGCC)_{exp}$. Chemical and enzymatic probing of $r(GGGGCC)_8$ indicate it adopts a hairpin structure in equilibrium with a quadruplex structure. Using this model, bioactive small molecules targeting $r(GGGGCC)_{exp}$ were designed and found to significantly inhibit RAN translation and foci formation in cultured cells expressing $r(GGGGCC)_{66}$ and neurons trans-differentiated from fibroblasts of repeat expansion carriers. Finally, we show that poly(GP) c9RAN proteins are specifically detected in c9ALS patient cerebrospinal fluid. Our findings highlight $r(GGGGCC)_{exp}$-binding small molecules as a possible c9FTD/ALS therapeutic, and suggest c9RAN proteins could potentially serve as a pharmacodynamic biomarker to assess efficacy of therapies that target $r(GGGGCC)_{exp}$.

2 Claims, 5 Drawing Sheets

Specification includes a Sequence Listing.

Related U.S. Application Data

(60) Provisional application No. 62/036,721, filed on Aug. 13, 2014.

(51) Int. Cl.
*A61K 31/404* (2006.01)
*C07D 471/04* (2006.01)
*C07D 209/14* (2006.01)
*C07D 209/42* (2006.01)
*A61K 31/7105* (2006.01)
*C07H 21/02* (2006.01)
*C12N 15/113* (2010.01)
*A61K 38/00* (2006.01)
*A61K 48/00* (2006.01)

(52) U.S. Cl.
CPC ......... *C07D 209/14* (2013.01); *C07D 209/42* (2013.01); *C07D 471/04* (2013.01); *C07H 21/02* (2013.01); *C12N 15/113* (2013.01); *A61K 38/00* (2013.01); *A61K 48/00* (2013.01); *C12N 2310/14* (2013.01)

(58) Field of Classification Search
USPC ........................................... 548/492; 514/419
See application file for complete search history.

1a-CA-biotin

SEQUENCE LISTING

```
<160> NUMBER OF SEQ ID NOS: 22

<210> SEQ ID NO 1
<211> LENGTH: 396
<212> TYPE: RNA
<213> ORGANISM: Artificial sequence
<220> FEATURE:
<223> OTHER INFORMATION: Synthetic sequence

<400> SEQUENCE: 1

ggggccgggg ccggggccgg ggccggggcc ggggccgggg ccggggccgg ggccggggcc     60

ggggccgggg ccggggccgg ggccggggcc ggggccgggg ccggggccgg ggccggggcc    120

ggggccgggg ccggggccgg ggccggggcc ggggccgggg ccggggccgg ggccggggcc    180

ggggccgggg ccggggccgg ggccggggcc ggggccgggg ccggggccgg ggccggggcc    240

ggggccgggg ccggggccgg ggccggggcc ggggccgggg ccggggccgg ggccggggcc    300

ggggccgggg ccggggccgg ggccggggcc ggggccgggg ccggggccgg ggccggggcc    360

ggggccgggg ccggggccgg ggccggggcc ggggcc                              396


<210> SEQ ID NO 2
<211> LENGTH: 48
<212> TYPE: RNA
<213> ORGANISM: Artificial sequence
<220> FEATURE:
<223> OTHER INFORMATION: Synthetic sequence

<400> SEQUENCE: 2

ggggccgggg ccggggccgg ggccggggcc ggggccgggg ccggggcc                  48


<210> SEQ ID NO 3
<211> LENGTH: 36
<212> TYPE: RNA
```

-continued

<213> ORGANISM: Artificial sequence
<220> FEATURE:
<223> OTHER INFORMATION: Synthetic sequence

<400> SEQUENCE: 3
cggcggcggc ggcggcggcg gcggcggcgg cggcgg 36

<210> SEQ ID NO 4
<211> LENGTH: 16
<212> TYPE: RNA
<213> ORGANISM: Artificial sequence
<220> FEATURE:
<223> OTHER INFORMATION: Synthetic sequence

<400> SEQUENCE: 4
ggccggccgg ccggcc 16

<210> SEQ ID NO 5
<211> LENGTH: 16
<212> TYPE: RNA
<213> ORGANISM: Artificial sequence
<220> FEATURE:
<223> OTHER INFORMATION: Synthetic sequence

<400> SEQUENCE: 5
ccccggcccc ggcccc 16

<210> SEQ ID NO 6
<211> LENGTH: 16
<212> TYPE: PRT
<213> ORGANISM: Artificial sequence
<220> FEATURE:
<223> OTHER INFORMATION: Synthetic sequence

<400> SEQUENCE: 6

Gly Pro Gly Pro Gly Pro Gly Pro Gly Pro Gly Pro Gly Pro Gly Pro
1 5 10 15

<210> SEQ ID NO 7
<211> LENGTH: 24
<212> TYPE: RNA
<213> ORGANISM: Artificial sequence
<220> FEATURE:
<223> OTHER INFORMATION: Synthetic sequence

<400> SEQUENCE: 7
ggggccgggg ccggggccgg ggcc 24

<210> SEQ ID NO 8
<211> LENGTH: 36
<212> TYPE: RNA
<213> ORGANISM: Artificial sequence
<220> FEATURE:
<223> OTHER INFORMATION: Synthetic sequence

<400> SEQUENCE: 8
ggggccgggg ccggggccgg ggccggggcc ggggcc 36

<210> SEQ ID NO 9
<211> LENGTH: 12
<212> TYPE: RNA
<213> ORGANISM: Artificial sequence
<220> FEATURE:
<223> OTHER INFORMATION: Synthetic sequence

<400> SEQUENCE: 9

-continued

```
ggggccgggg cc                                                          12


<210> SEQ ID NO 10
<211> LENGTH: 120
<212> TYPE: RNA
<213> ORGANISM: Artificial sequence
<220> FEATURE:
<223> OTHER INFORMATION: Synthetic sequence

<400> SEQUENCE: 10

ggggccgggg ccggggccgg ggccggggcc ggggccgggg ccggggccgg ggccggggcc      60

ggggccgggg ccggggccgg ggccggggcc ggggccgggg ccggggccgg ggccggggcc     120


<210> SEQ ID NO 11
<211> LENGTH: 180
<212> TYPE: RNA
<213> ORGANISM: Artificial sequence
<220> FEATURE:
<223> OTHER INFORMATION: Synthetic sequence

<400> SEQUENCE: 11

cggcggcggc ggcggcggcg gcggcggcgg cggcggcggc ggcggcggcg gcggcggcgg      60

cggcggcggc ggcggcggcg gcggcggcgg cggcggcggc ggcggcggcg gcggcggcgg     120

cggcggcggc ggcggcggcg gcggcggcgg cggcggcggc ggcggcggcg gcggcggcgg     180


<210> SEQ ID NO 12
<211> LENGTH: 264
<212> TYPE: RNA
<213> ORGANISM: Artificial sequence
<220> FEATURE:
<223> OTHER INFORMATION: Synthetic sequence

<400> SEQUENCE: 12

cggcggcggc ggcggcggcg gcggcggcgg cggcggcggc ggcggcggcg gcggcggcgg      60

cggcggcggc ggcggcggcg gcggcggcgg cggcggcggc ggcggcggcg gcggcggcgg     120

cggcggcggc ggcggcggcg gcggcggcgg cggcggcggc ggcggcggcg gcggcggcgg     180

cggcggcggc ggcggcggcg gcggcggcgg cggcggcggc ggcggcggcg gcggcggcgg     240

cggcggcggc ggcggcggcg gcgg                                            264


<210> SEQ ID NO 13
<211> LENGTH: 23
<212> TYPE: DNA
<213> ORGANISM: Artificial sequence
<220> FEATURE:
<223> OTHER INFORMATION: Synthetic sequence

<400> SEQUENCE: 13

gggccctatt ctatagtgtc acc                                              23


<210> SEQ ID NO 14
<211> LENGTH: 19
<212> TYPE: DNA
<213> ORGANISM: Artificial sequence
<220> FEATURE:
<223> OTHER INFORMATION: Synthetic sequence

<400> SEQUENCE: 14

acaacagatg gctggcaac                                                   19


<210> SEQ ID NO 15
<211> LENGTH: 20
```

<212> TYPE: DNA
<213> ORGANISM: Artificial sequence
<220> FEATURE:
<223> OTHER INFORMATION: Synthetic sequence

<400> SEQUENCE: 15
gtaacccgtt gaaccccatt 20

<210> SEQ ID NO 16
<211> LENGTH: 20
<212> TYPE: DNA
<213> ORGANISM: Artificial sequence
<220> FEATURE:
<223> OTHER INFORMATION: Synthetic sequence

<400> SEQUENCE: 16
ccatccaatc ggtagtagcg 20

<210> SEQ ID NO 17
<211> LENGTH: 18
<212> TYPE: DNA
<213> ORGANISM: Artificial sequence
<220> FEATURE:
<223> OTHER INFORMATION: Synthetic sequence

<400> SEQUENCE: 17
cctggcaccc agcacaat 18

<210> SEQ ID NO 18
<211> LENGTH: 18
<212> TYPE: DNA
<213> ORGANISM: Artificial sequence
<220> FEATURE:
<223> OTHER INFORMATION: Synthetic sequence

<400> SEQUENCE: 18
gggccggact cgtcatac 18

<210> SEQ ID NO 19
<211> LENGTH: 16
<212> TYPE: PRT
<213> ORGANISM: Artificial sequence
<220> FEATURE:
<223> OTHER INFORMATION: Synthetic sequence

<400> SEQUENCE: 19

```
Gly Ala Gly Ala Gly Ala Gly Ala Gly Ala Gly Ala Gly Ala Gly Ala
1               5                   10                  15
```

<210> SEQ ID NO 20
<211> LENGTH: 16
<212> TYPE: PRT
<213> ORGANISM: Artificial sequence
<220> FEATURE:
<223> OTHER INFORMATION: Synthetic sequence

<400> SEQUENCE: 20

```
Gly Arg Gly Arg Gly Arg Gly Arg Gly Arg Gly Arg Gly Arg Gly Arg
1               5                   10                  15
```

<210> SEQ ID NO 21
<211> LENGTH: 16
<212> TYPE: PRT
<213> ORGANISM: Artificial sequence
<220> FEATURE:
<223> OTHER INFORMATION: Synthetic sequence -continued

```
<400> SEQUENCE: 21

Pro Ala Pro Ala Pro Ala Pro Ala Pro Ala Pro Ala Pro Ala Pro Ala
1               5                   10                  15


<210> SEQ ID NO 22
<211> LENGTH: 16
<212> TYPE: PRT
<213> ORGANISM: Artificial sequence
<220> FEATURE:
<223> OTHER INFORMATION: Synthetic sequence

<400> SEQUENCE: 22

Pro Arg Pro Arg Pro Arg Pro Arg Pro Arg Pro Arg Pro Arg Pro Arg
1               5                   10                  15
```

TREATMENT OF C9FTD/ALS BY TARGETING RNA EXPANDED REPEAT SEQUENCES

CROSS-REFERENCE TO RELATED APPLICATION

This application claims the priority of U.S. provisional application Ser. No. 62/036,721, filed Aug. 13, 2014, the disclosure of which is incorporated by reference herein in its entirety.

STATEMENT OF GOVERNMENT SUPPORT

This invention was made with government support under GM097455 awarded by the National Institutes of Health. The government has certain rights in the invention.

BACKGROUND

Frontotemporal dementia (FTD) and amyotrophic lateral sclerosis (ALS) are overlapping neurodegenerative diseases with no effective treatment. Success in developing a treatment will require a well-orchestrated effort that addresses multiple aspects of the drug discovery process, including target identification and validation, as well as the identification of biomarkers to assess efficacy of potential therapies in clinical trials. These endeavors have been hampered by an incomplete understanding of FTD and ALS pathogenesis. However, with the discovery that a GGGGCC repeat expansion in C9ORF72 is the most common genetic cause of FTD and ALS (DeJesus-Hernandez et al., 2011; Renton et al., 2011), a new therapeutic target has come to light.

Two putative pathomechanisms of "c9FTD/ALS" involve RNA transcribed from the expansion. First, these transcripts (termed $r(GGGGCC)_{exp}$) may cause toxicity through the formation of nuclear RNA foci that sequester various RNA-binding proteins [for review, see (Gendron et al , 2014)]. Second, $r(GGGGCC)_{exp}$ undergoes repeat associated non-ATG (RAN) translation producing "c9RAN proteins" that form neuronal inclusions throughout the central nervous system (Ash et al., 2013; Mori et al., 2013b). Consequently, neutralizing or degrading $r(GGGGCC)_{exp}$ holds promise as a therapeutic approach for c9FTD/ALS. Indeed, antisense oligonucleotides to C9ORF72 transcripts suppress features associated with the repeat expansion in human induced pluripotent stem cell-derived neurons (Donnelly et al., 2013; Sareen et al., 2013). In light of pharmacological advantages, small molecules may offer an attractive option for targeting $r(GGGGCC)_{exp}$. Capitalizing on our findings that $r(GGGGCC)_n$ adopts a hairpin structure in addition to a G-quadruplex one, we designed small molecules able to bind $r(GGGGCC)_{exp}$ and to significantly decrease RAN translation and foci formation in cultured cells expressing $r(GGGGCC)_{66}$ (SEQ ID NO:1) and in induced neurons (iNeurons) directly converted from fibroblasts of C9ORF72 repeat expansion carriers. These findings indicate that designer small molecules targeting $r(GGGGCC)_{exp}$ may prove promising as a c9FTD/ALS therapeutic. Furthermore, since we found that poly(GP) c9RAN proteins are detected in c9ALS cerebrospinal fluid (CSF), poly(GP) proteins may serve as a pharmacodynamic biomarker to assess efficacy of potential therapies that target $r(GGGGCC)_{exp}$.

SUMMARY

The invention is directed, in various embodiments, to small molecules targeting the RNA expanded repeat sequence $r(GGGGCC)_{exp}$ and to the use of the compounds to significantly decrease RAN translation and foci formation in cultured cells expressing $r(GGGGCC)_{66}$ (SEQ ID NO:1) and in induced neurons (iNeurons) directly converted from fibroblasts of C9ORF72 repeat expansion carriers.

In various embodiments, the invention provides a compound of formula

1a

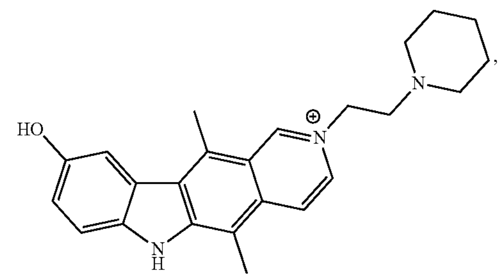

2

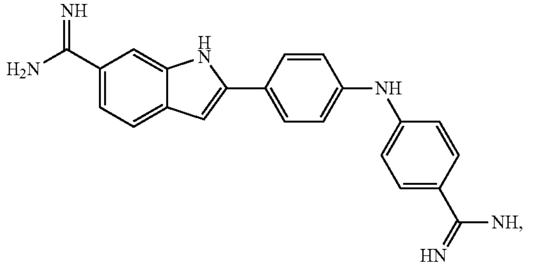

or

3

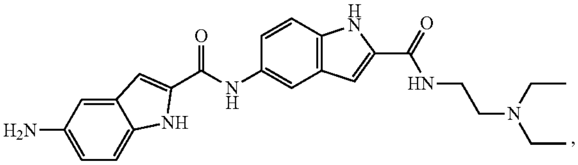

or a pharmaceutically acceptable salt thereof.

In various embodiments, the invention provides a method of inhibiting repeat-associated non-ATG (RAN) translation and foci formation in cultured cells expressing $r(GGGGCC)_{66}$ (SEQ ID NO:1) and neurons trans-differentiated from fibroblasts of repeat expansion carriers, comprising contacting the cells with an effective amount of a compound of formula 1a, 2, or 3, or a pharmaceutically acceptable salt thereof.

In various embodiments, the invention provides a method of treating a patient afflicted with ALS, comprising administering to the patient an effective dose of a compound of formula 1a, 2, or 3, or a pharmaceutically acceptable salt thereof.

BRIEF DESCRIPTION OF THE FIGURES

Synthetic route (FIG. 2A) and analytic HPLC chromatogram (FIG. 2B) for 1a-CA-Biotin.

Human Fibroblasts are Converted to iNeurons Following PTB1 Knockdown.

Representative bright field images show cell morphology upon control, non-silencing shRNA and shPTB1 transduction of human fibroblasts. While the cells infected with control shRNA retained their fibroblast-like shape, shPTB1-transduction induced a neuronal morphology with reduced size of cell soma, and neurite outgrowth. Scale bar, 400 μm.

Validation of Poly(GP) MSD Sandwich Immunoassay.

Figure 4A:
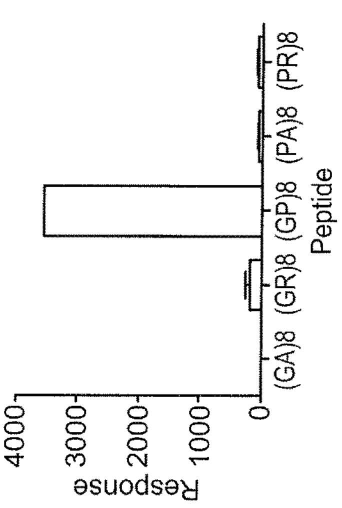
Figure 4B:
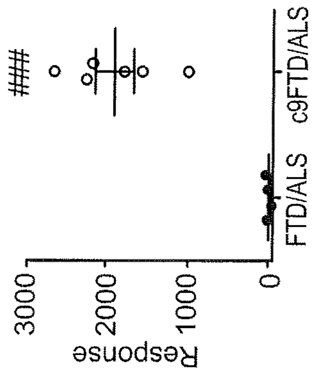
Figure 4C:
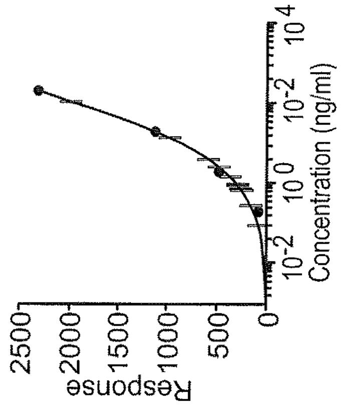

FIG. 4A) A sandwich MSD immunoassay using rabbit polyclonal anti-GP was developed. To validate specificity, synthetic peptides representing each possible c9RAN protein translated from sense or antisense transcripts of the expanded C9ORF72 repeat were diluted in Tris-buffered saline (TBS) and assayed (200 ng/ml, 50 μl per well in duplicate wells). Response values correspond to intensity of emitted light upon electrochemical stimulation of the assay plate using the MSD Sector Imager 2400, from which the background response in wells containing only TBS was subtracted. FIG. 4B) Poly(GP) protein expression in frontal cortical homogenates from 6 c9FTD/ALS patients and 4 patients without the C9ORF72 repeat expansion were analyzed by poly(GP) MSD immunoassay. Response values correspond to the intensity of emitted light upon electrochemical stimulation of the assay plate, from which the average background response measured in brain lysates lacking the C9ORF72 mutation was subtracted. ###P=0.0002 (non-paired, two-tailed t test). FIG. 4C) Standard curve using (GP)$_8$ (SEQ ID NO:6) peptide as the calibrator. A sigmoidal dose-response nonlinear regression was used to fit log(dose) vs. response curve using Prism 5 software. Vertical lines indicate interpolated concentration of poly(GP) in c9ALS CSF.

DETAILED DESCRIPTION

Highlights:

Certain of the highlights of the present invention include the findings that:

1. (GGGGCC)$_{exp}$ RNA forms a hairpin structure in equilibrium with a G-quadruplex structure.
2. Neurons directly converted from C9ORF72+ fibroblasts express c9RAN proteins and foci.
3. Small molecule binders of (GGGGCC)$_{exp}$ RNA ameliorate c9FTD/ALS-associated defects.
4. c9RAN proteins are detected in c9ALS patient cerebrospinal fluid.

r(GGGGCC)$_8$ Preserves a Hairpin Structure with Periodically Repeating 1×1 Nucleotide GG Internal Loops in Equilibrium with a G-Quadruplex With the goal of designing small molecule modulators of r(GGGGCC), we investigated its structure. Using evidence from gel mobility shift assays and spectroscopic methods, previous reports suggest r(GGGGCC) forms intra- and inter-molecular G-quadruplex structures (Fratta et al., 2012; Reddy et al., 2013), with another suggesting r(GGGGCC) repeats adopt both G-quadruplex and hairpin structures (Haeusler et al., 2014). To further probe the structure of r(GGGGCC), we completed spectroscopic (circular dichroism (CD) and optical melting), chemical (modification with dimethyl sulfate (DMS)), and enzymatic analyses. CD studies of r(GGGGCC)$_4$(SEQID NO:7), r(GGGGCC)$_6$ (SEQID NO:8) and r(GGGGCC)$_8$ (SEQID NO:2) revealed these RNAs likely fold into a G-quadruplex structure in the presence of $K^+$ but not $Na^+$, which promotes a hairpin structure. We next studied the structures of r(GGGGCC) by optical melting, as G-quadruplexes have signature melting curves (large hypochromic transition of UV absorbance at 295 nm) (Mergny et al., 1998). In agreement with CD studies, optical melts completed in the presence of $Na^+$ indicated that $r(GGGGCC)_4$ (SEQID NO:6), $r(GGGGCC)_6$ (SEQID NO:7) and $r(GGGGCC)_8$ (SEQID NO:2) form intramolecular hairpins. In contrast, optical melts completed in the presence of $K^+$ indicate the presence of both hairpin and G-quadruplex structures (Table 1).

TABLE 1

| Thermodynamic properties of $r(GGGGCC)_n$ repeats | | | | |
|---|---|---|---|---|
| Oligo nucleotides | ΔH (kcal/mol) | ΔS (cal/K · mol) | ΔG (kcal/mol, 37° C.) | $T_m$ (°C., 100 μM) |
| $r(GGGGCC)_4$[a] | -54.5 ± 1.7 | -158 ± 5 | -5.69 ± 0.23 | 73.5 ± 0.6 |
| $r(GGGGCC)_6$[a] | -61.9 ± 2.0 | -175 ± 6 | -7.54 ± 0.08 | 79.8 ± 0.3 |
| $r(GGGGCC)_8$[a] | -69.4 ± 0.8 | -194 ± 2 | -9.26 ± 0.14 | 81.0 ± 0.5 |
| $r(GGGGCC)_8$[b] | — | — | — | — |

[a]RNA samples were heated at 95° C. in 10 mM Tris HCl buffer, pH 7.4 and 100 mM NaCl prior to completing optical melting experiments.

[b]RNA samples were heated at 95° C. in 10 mM Tris HCl buffer, pH 7.4 and 100 mM KCl prior to completing optical melting experiments, the RNA was too stable to observe melting at highest temperature tested (95° C.) and thermodynamic parameters were not calculated. All data was recorded in duplicate and presented as mean ± SD.

The folding of $r(GGGGCC)_8$ (SEQID NO:2) was next examined using enzymatic and chemical mapping in the presence of $Li^+$ or $K^+$, the latter known to stabilize G-quadruplex formation (Hardin et al., 1992). Enzymatic mapping revealed an alternating pattern of cleavage by enzymes that specifically cleave paired or non-canonically paired nucleotides, suggesting that some populations form a hairpin structure. These findings were confirmed using the chemical modification reagent DMS.

We additionally explored the structure of $r(GGGGCC)_8$ (SEQID NO:2) by analyzing its 1D $^1H$ NMR spectra. At low annealing temperatures, the NMR spectra indicate $r(GGGGCC)_8$ folds into a hairpin with non-canonically paired Gs in the stem (spectrum collected at 37° C.). As the annealing temperature increases, however, NMR peaks become broad, indicating increased population of a G-quadruplex. The existence of both conformations is not surprising as other studies have suggested RNAs that form quadruplexes can form alternative structures, including hairpins (Bugaut et al., 2012).

Identification of Small Molecules that Bind $r(GGGGCC)_{exp}$

Exploiting the findings above, we sought to identify small molecules that bind $r(GGGGCC)_{exp}$ and determine whether they improve c9FTD/ALS-associated defects. It was reported that TMPyP4, a known G-quadruplex binder, binds $r(GGGGCC)_8$ in vitro (Zamiri et al., 2014). Although the bioactivity of TMPyP4 was not explored, these studies suggest it is indeed possible to identify small molecules that bind r(GGGGCC) repeats. We previously developed a strategy to design small molecules that bind an RNA target using information about RNA-small molecule interactions (Velagapudi et al., 2014). Small molecule leads can be further optimized by chemical similarity searching, which identifies compounds that are chemically similar to the leads. We reported that small molecule 1a binds 1×1 GG internal loops present in $r(CGG)_{exp}$ and improves fragile X-associated tremor/ataxia syndrome (FXTAS)-associated defects (Disney et al., 2012). Given the structural similarity between $r(CGG)_{exp}$ and $r(GGGGCC)_{exp}$, we hypothesized that 1a and compounds chemically similar to it might bind $r(GGGGCC)_{exp}$. We collected 132 such small molecules and screened them for binding to $r(GGGGCC)_8$. Three lead compounds (1a, 2 and 3) were identified (FIG. 1A; Table 2) and further characterized.

TABLE 2

| Compounds screened for displacing TO-PRO-1 from $r(GGGGCC)_8$ (SEQ ID NO: 2) at different concentrations. | | | | | |
|---|---|---|---|---|---|
| NSC Identifier | Manuscript ID | NSC Identifier | Manuscript ID | NSC Identifier | Manuscript ID |
| 311153 | 1a | 51189 | 12 | 211726 | 23 |
| 377363 | 2 | 63676 | 13 | 215651 | 24 |
| 699145 | 3 | 66751 | 14 | 220278 | 25 |
| 642 | 4 | 66759 | 15 | 283167 | 26 |
| 17602 | 5 | 66761 | 16 | 305831 | 27 |
| 536 | 6 | 77880 | 17 | 305836 | 28 |
| 35849 | 7 | 114702 | 18 | 322921 | 29 |
| 38278 | 8 | 119095 | 19 | 357775 | 30 |
| 41609 | 9 | 128584 | 20 | 369715 | 31 |

TABLE 2-continued

Compounds screened for displacing TO-PRO-1 from r(GGGGCC)$_8$ (SEQ ID NO: 2) at different concentrations.

| NSC Identifier | Manuscript ID | NSC Identifier | Manuscript ID | NSC Identifier | Manuscript ID |
|---|---|---|---|---|---|
| 50464 | 10 | 128801 | 21 | 408148 | 32 |
| 50467 | 11 | 173329 | 22 | | |

Kinetic binding studies showed that 1a, 2, and 3 bind to r(GGGGCC)$_8$ (SEQID NO:2) with $K_d$'s of 9.7, 10, and 16 μM, respectively, similar to those observed for r(CGG)$_{12}$. In contrast, 1a, 2, and 3 bind more weakly to a hairpin with a fully paired stem, suggesting the compounds are at least modestly selective (FIG. 1B). We perturbed the equilibrium between hairpin and G-quadruplex structures by folding r(GGGGCC)$_8$ (SEQID NO:2) in the presence of an additional 100 mM NaCl (favors hairpin) or KCl (favors quadruplex). The observed $K_d$'s for 1a and 3 were 3- to 10-fold weaker in the presence of $Na^+$ and $K^+$, indicating that ionic strength affects binding. Of interest, the affinity of 2 for r(GGGGCC)$_8$ (SEQID NO:2) was not significantly affected by addition of $Na^+$, but became >6-fold weaker in $K^+$. These results indicate that compound 2 recognizes the hairpin structure over the G-quadruplex (FIG. 1B).

Given that small molecule binders of r(GGGGCC)$_{exp}$ may influence the thermodynamic stability of the RNA, which could in turn influence foci formation and RAN translation, optical melting was used to study whether compounds increase r(GGGGCC)$_8$ (SEQID NO:2) stability. While compound 3 did not significantly affect r(GGGGCC)$_8$'s (SEQID NO:2) stability or melting temperature, 1a and 2 stabilized the RNA by 0.95 and 0.63 kcal/mol, respectively, and increased the $T_m$ by 3.1 and 1.9° C., respectively (FIG. 1C & Table 3).

TABLE 3

Thermodynamic properties of r(GGGGCC)8 (SEQ ID NO: 2) with lead compounds.

| Samples[a] | ΔH (kcal/mol) | ΔS (cal/K · mol) | ΔG (kcal/mol, 37° C.) | $T_m$ (°C., 100 μM) |
|---|---|---|---|---|
| r(GGGGCC)$_8$ | -71.4 ± 1.4 | -201 ± 4 | -8.98 ± 0.15 | 81.6 ± 0.3 |
| r(GGGGCC)$_8$ + 1a | -74.4 ± 1.0 | -208 ± 3 | -9.93 ± 0.15 | 84.7 ± 0.2 |
| r(GGGGCC)$_8$ + 2 | -73.6 ± 0.4 | -206 ± 1 | -9.61 ± 0.07 | 83.5 ± 0.1 |
| r(GGGGCC)$_8$ + 3 | -71.1 ± 1.5 | -200 ± 4 | -9.10 ± 0.24 | 82.2 ± 0.2 |

[a]RNA samples (1 uM) were heated at 95° C. in 10 mM Tris HCl buffer, pH 7.4 and 100 mM NaCl and cooled to room temperature, followed by addition of the compound (3 μM), then the optical melting experiments were performed. All data was recorded in duplicate and presented as mean ± SD.

Figure 2A:
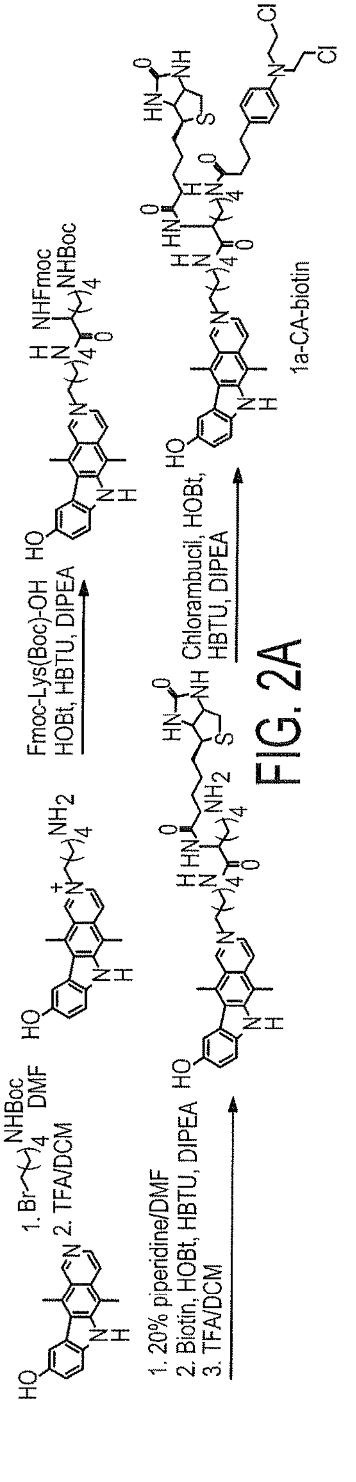
FIG. 2C) (GGGGCC)$_{66}$ (SEQ ID NO:1)—expressing cells were treated with DMSO or compounds 1a (25, 50 and 100 μM) for 24 h. Poly(GP) protein expression in cell lysates was analyzed by GP immunoassay. Responses correspond to the intensity of emitted light upon electrochemical stimulation of the assay plate using the MSD Sector Imager 2400, normalized to the response in DMSO-treated cells. Data presented as mean+SEM (n=3). P<0.01, *P<0.001 as assessed by one-way ANOVA followed by Dunnett's Multiple Comparison Test.
FIG. 2D) To determine whether the decrease in the percentage of foci-positive r(GGGGCC)$_{66}$ (SEQ ID NO:1)—expressing cells following 1a treatment is caused by inhibition of foci formation or is instead an artefact resulting from impaired binding of the FISH probe to 1a-bound r(GGGGCC)$_{66}$ (SEQ ID NO:1), non-treated (GGGGCC)$_{66}$ (SEQ ID NO:1)—expressing cells were fixed prior to conducting RNA-FISH with a probe co-incubated with either DMSO or 1a. Note that la did not interfere with binding of the probe to r(GGGGCC)$_{66}$ (SEQ ID NO:1)—containing foci.
FIG. 2E) A sandwich MSD immunoassay using rabbit polyclonal anti-PR was developed. To validate specificity, lysates from cells expressing the indicated GFP-tagged dipeptide repeat proteins were assayed. Response values correspond to intensity of emitted light upon electrochemical stimulation of the assay plate using the MSD Sector Imager 2400, from which the background response in wells containing lysates from GFP-expressing cells was subtracted.
Figure 2B:
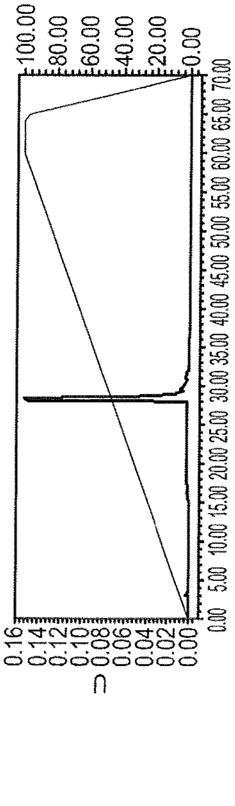

Small Molecule Binders of r(GGGGCC)$_{exp}$ Inhibit RAN Translation and Foci Formation in (GGGGCC)$_{66}$ (SEQID NO:1)-Expressing Cells To determine whether compounds 1a, 2 and 3 bind r(GGGGCC)$_{exp}$ in cells, we employed HEK293 cells transfected to express 66 GGGGCC repeats with no upstream ATG, and our previously reported strategy to identify cellular targets of a small molecule. In this strategy, small molecules are conjugated to: (i) a reactive module that forms a covalent cross-link with the target (chlorambucil; CA); and (ii) biotin for facile isolation of small molecule-biomolecule adducts (Guan and Disney, 2013). First, a biotin-chlorambucil conjugate of la was synthesized (1a-CA-biotin; FIG. 2A, B), added to (GGGGCC)$_{66}$ (SEQID NO:1)—expressing cells, and allowed to react with its cellular targets. Biomolecule-small molecule adducts were then isolated with streptavidin-functionalized resin. qRT-PCR analysis of the isolated fractions showed an 80-fold enrichment of r(GGGGCC)$_{66}$ compared to 18S rRNA (normalized to untreated lysate). To determine whether 1a, 2 and 3 bind r(GGGGCC)$_{exp}$ directly, we completed a competitive profiling experiment by co-treating (GGGGCC)$_{66}$ (SEQID NO:1)—expressing cells with 1a-CA-biotin and the compound of interest. That is, the targets of 1a, 2 and 3 can be inferred by their depletion in pull-down fractions. Indeed, the amount of r(GGGGCC)$_{66}$ (SEQID NO:1) that forms an adduct with 1a-CA-biotin was significantly depleted in the presence of each compound (FIG. 2B).

Figure 2C:
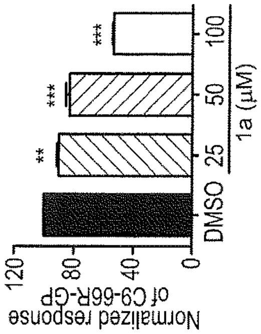

Having established that all three compounds bind r(GGGGCC)$_{66}$ (SEQID NO:1), we evaluated their effect on RAN translation. While no evidence of RAN translation was seen in cells expressing short (GGGGCC)$_2$ (SEQID NO:9) and (GGGGCC)$_{20}$ (SEQID NO:10) repeats, expression of (GGGGCC)$_{66}$ (SEQID NO:1) resulted in the synthesis of poly(GP) and poly(GA) proteins, but not poly(GR) proteins (not shown). Compound 3 (100 μM, 24 h) modestly inhibited synthesis of poly(GP) proteins, but did not influence poly(GA) protein production. In contrast, compounds 1a and 2 significantly decreased both poly(GP) and poly(GA) protein levels). Given that 1a and 2 have similar effects on RAN translation, and that 1a also inhibits this event in iNeurons (as shown below), we tested additional concentrations of 1a and found it affords a dose-dependent effect on RAN translation; statistically significant decreases in poly(GP) protein of 10%, 18% and 47% were detected by immunoassay of lysates from (GGGGCC)$_{66}$ (SEQID NO:1)-expressing cells treated with 25, 50 or 100 μM, respectively (FIG. 2C).

Figure 2D:
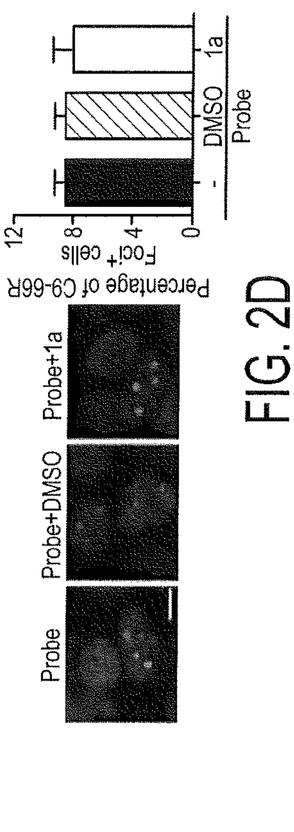

In addition to the accumulation of c9RAN proteins, nuclear foci are detected in (GGGGCC)$_{66}$ (SEQID NO:1)-expressing cells. Consistent with the effect of r(GGGGCC)$_{exp}$-binding compounds on RAN translation, 1a and 2, but not 3, significantly decreased the percentage of foci-positive cells. This was likely caused by inhibition of foci formation and not a result of impaired binding of the probe to r$(GGGGCC)_{66}$ (SEQID NO:1) in the presence of compound, given that conducting RNA-FISH on fixed, non-treated $(GGGGCC)_{66}$-expressing cells with a probe co-incubated with la did not prevent detection of foci (FIG. 2D).

Figure 2E:
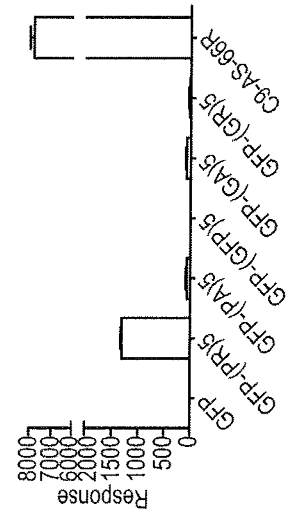

Since the C9ORF72 repeat expansion is bidirectionally transcribed in c9FTD/ALS, and since antisense transcripts containing (CCCCGG) repeats are also RAN translated and form foci (Gendron et al., 2013; Mori et al., 2013a; Zu et al., 2013), we evaluated the effect of 1a in r$(CCCCGG)_{66}$-expressing cells previously shown to express poly(PR) and poly(GP) proteins (Gendron et al., 2013). Whereas 1a (100 μM, 24 h) significantly decreased poly(GP) proteins RAN translated from sense transcripts), it had no effect on poly (GP) or poly(PR) proteins RAN translated from antisense r$(GGGGCC)_{66}$ (SEQID NO:1), as assessed by immunoassay (see FIG. 2E and FIG. 4A for PR and GP assay validation, respectively). Likewise, no change in the percentage of cells bearing r(CCCCGG) foci was detected following 1a treatment. In contrast, we reported that 1a does reduce nuclear foci in r(CGG)60 (SEQ ID NO:11)—expressing cells (Disney et al., 2012), and we show here that 1a also inhibits RAN translation in cells expressing $(CGG)_{88}$ (SEQ ID NO:12) placed in the 5'UTR of GFP, but does not affect downstream canonical translation. These results confirm the structural similarity between r$(CGG)_{exp}$ and r$(GGGGCC)_{exp}$ in cells, and selectivity of 1a towards this structure.

Figure 3A:
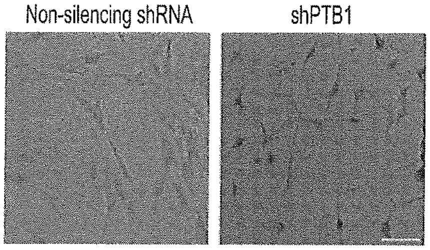
FIG. 3A)
Figure 3B:
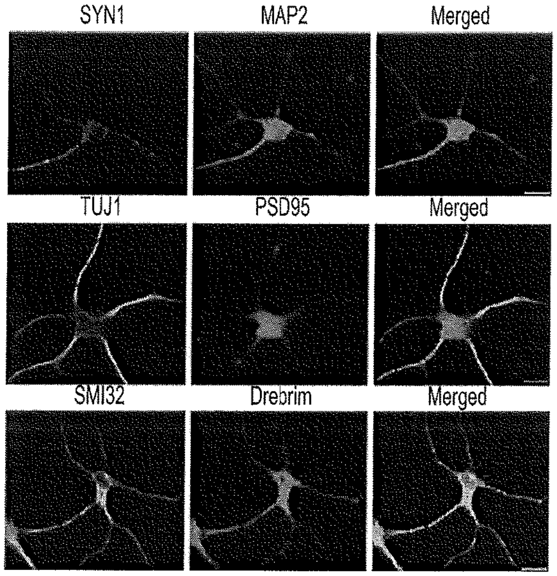
FIG. 3B) iNeurons express cytoskeletal neuronal markers MAP2, TUJ1 and neurofilament Smi32, as well as synaptic markers synapsin 1 (SYN1) and post-synaptic density protein 95 (PSD95). These cells also express Drebrin, which plays a role in the formation and maintenance of dendritic spines in neurons. Scale bars, 20 μm.
Figure 3C:
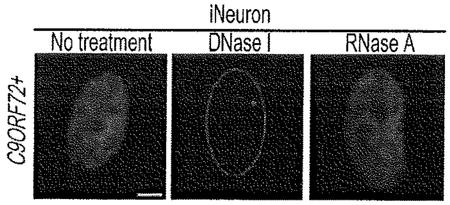
FIG. 3C) Nuclear foci detected in C9ORF72+ iNeurons are primarily composed of RNA. C9ORF72+ iNeurons were treated with DNase I or RNase A prior to RNA FISH using a 5'TYE563-(CCCCGG)$_{2.5}$-'3 (SEQ ID NO:5) LNA probe. Treatment with RNAse A degraded all foci, but DNAse I only degraded nuclear DNA (observed by loss of Hoechst staining) leaving foci in iNeurons intact. Scale bars, 5 μm.
Figure 3D:
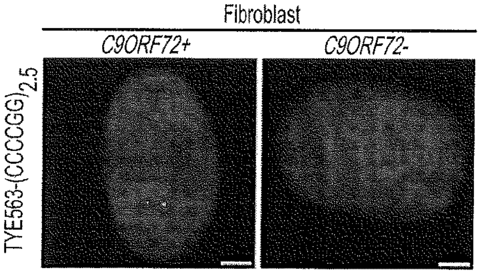
FIG. 3D) As observed in C9ORF72+ iNeurons foci of (GGGGCC) repeat-containing RNA were detected in fibroblasts from individuals with the C9ORF72 repeat expansion. Scale bars, 5 μm.
Figure 3E:
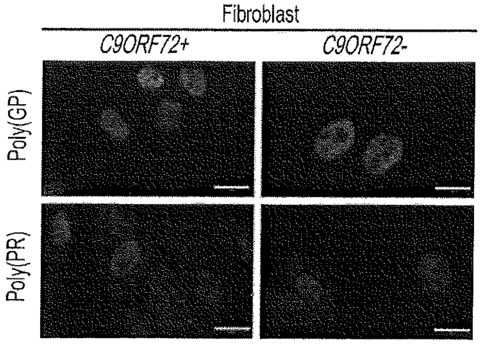
FIG. 3E) In contrast to C9ORF72+ iNeurons, poly (GP) and poly(PR) protein inclusions are not observed in C9ORF72+ fibroblasts. Scale bars, 20 μm.
Figure 3F:
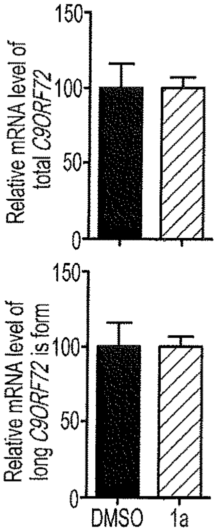
FIG. 3F) qRT-PCR using primers designed to target all C9ORF72 variants, or specifically the long form of C9ORF72, show that treatment of iNeurons with 1a (4 μM) does not cause a decrease in these mRNA transcripts. Data presented as mean+SEM of three C9ORF72+ iNeurons lines analyzed by paired t-test.
Figure 3G:
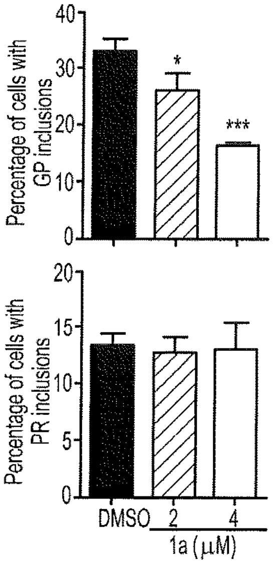
FIG. 3G) A dose-dependent decrease in poly(GP) inclusions, but not poly(PR) inclusions, was observed upon treatment of C9ORF72+ iNeurons with 1a. Data presented as mean+SEM (n=3). *P<0.05, ***P<0.001, as assessed by one-way ANOVA followed by Dunnett's Multiple Comparison Test. Nuclei (blue) in all panels were stained with Hoechst 33258.

Small Molecule Binders of r(GGGGCC) Inhibit RAN Translation and Foci Formation in $(GGGGCC)_{exp}$-expressing iNeurons To establish a more physiological disease cell model, fibroblasts with or without the C9ORF72 repeat expansion were directly converted to a neuronal lineage by repressing polypyrimidine-tract-binding protein (PTB1), as recently described (Xue et al., 2013). PTB1 depletion caused fibroblasts to adopt a neuronal morphology with reduced soma size and neurite formation (FIG. 3A). These iNeurons expressed neuronal and synaptic markers, including MAP2, TUJ1, PSD95, Synapsin I and Drebrin (FIG. 3B). Nuclear foci, degraded by RNase A but resistant to DNase I (FIG. 3C), were present in both C9ORF72+ fibroblasts (FIG. 3D) and iNeurons. Cytoplasmic poly(GP) inclusions, as well as poly(PR) inclusions, were also present in C9ORF72+ iNeurons, but were not found in parental fibroblasts (FIG. 3E). No foci or poly(GP) inclusions were detected in iNeurons lacking the expanded repeat. Of importance, in three C9ORF72+ iNeuron lines, compound la significantly decreased the percentage of cells with RNA foci, and poly(GP) inclusions, while having no effect on C9ORF72 mRNA levels (FIG. 3F). Consistent with findings in $(GGGGCC)_{66}$ (SEQ ID NO:1)—expressing cells, a dose-dependent decrease in RAN translation of poly(GP) was observed in la-treated C9ORF72+ iNeurons, but no change in poly(PR) expression, which is synthesized from the antisense transcript, was detected (FIG. 3G). Due to toxicity associated with compound 2 in iNeurons, its effect on RAN translation and foci formation could not be reliably tested. Taken together, our data indicate that our strategy to design small molecule modulators of r(GGGGCC) led to the successful identification of a compound that mitigates abnormal events initiated by r$(GGGGCC)_{exp}$.

Poly(GP) Proteins are Detected in c9ALS CSF

Our findings above indicate that r$(GGGGCC)_{exp}$-targeting small molecules can inhibit foci formation and RAN translation. Consequently, if c9RAN proteins are detected in CSF, they have the potential to serve as a measurable indicator of therapeutic efficacy. To test this notion, we developed an immunoassay that specifically detects poly(GP) proteins (FIG. 4A), and validated it as a sensitive means to measure endogenous poly(GP) using soluble fractions of frontal cortex tissues. As expected, poly(GP) was specifically detected in c9FTD/ALS samples using this assay (FIG. 4B).

To test poly(GP) proteins as clinically relevant biomarkers, we evaluated whether they are also detectable in CSF. We analyzed CSF from 14 c9ALS patients in comparison to CSF from 25 ALS patients without the C9ORF72 mutation and 5 healthy subjects (see Table 4 for patient details). Poly(GP) proteins were detected only in c9ALS CSF. Using a $(GP)_8$ peptide standard curve, we estimate the median concentration of CSF poly(GP) in the c9ALS cases to be 0.67 ng/ml (FIG. 4C, Table 4). These exciting findings provide an important first step in identifying pharmacodynamic biomarkers for c9FTD/ALS.

TABLE 4

Patient Information

| | C9ORF72 Repeat Expansion | Sample Number | Gender | Age at onset | Age at CSF collection | Estimated [poly(GP)] (ng/ml) |
|---|---|---|---|---|---|---|
| ALS | Yes | 1 | M | 54 | 56 | 0.71 |
| | Yes | 2 | M | 49 | 50 | 2.49 |
| | Yes | 3 | F | 49 | 50 | 97.64 |
| | Yes | 4 | M | 56 | 56 | 11.36 |
| | Yes | 5 | M | 58 | 59 | 0.12 |
| | Yes | 6 | M | 59 | 60 | 0.02 |
| | Yes | 7 | F | 48 | 48 | 0.42 |
| | Yes | 8 | M | 42 | 43 | 1.03 |
| | Yes | 9 | F | 53 | 54 | 1.09 |
| | Yes | 10 | F | 63 | 64 | 0.60 |
| | Yes | 11 | F | 60 | 60 | 0.13 |
| | Yes | 12 | F | 46 | 48 | 3.14 |
| | Yes | 13 | F | 54 | 57 | 0.64 |
| | Yes | 14 | F | 53 | 54 | 0.63 |
| | No | 15 | M | 54 | 59 | — |
| | No | 16 | M | 45 | 47 | — |
| | No | 17 | F | 48 | 52 | — |
| | No | 18 | M | 57 | 58 | — |
| | No | 19 | F | 50 | 52 | — |
| | No | 20 | M | 65 | 67 | — |
| | No | 21 | M | 59 | 64 | — |
| | No | 22 | M | 57 | 59 | — |
| | No | 23 | M | 65 | 66 | — |
| | No | 24 | M | 74 | 76 | — |
| | No | 25 | F | 50 | 51 | — |
| | No | 26 | F | 64 | 64 | — |
| | No | 27 | F | 65 | 66 | — |
| | No | 28 | F | 29 | 29 | — |
| | No | 29 | M | 52 | 53 | — |
| | No | 30 | M | 36 | 42 | — |
| | No | 31 | F | 53 | 57 | — |
| | No | 32 | M | 59 | 60 | — |
| | No | 33 | F | 55 | 61 | — |
| | No | 34 | M | 55 | 55 | — |
| | No | 35 | M | 45 | 49 | — |
| | No | 36 | M | 65 | 65 | — |
| | No | 37 | F | 62 | 63 | — |
| | No | 38 | M | 49 | 50 | — |
| | No | 39 | M | 76 | 78 | — |
| healthy | No | 40 | M | — | 68 | — |
| | No | 41 | M | — | 54 | — |
| | No | 42 | F | — | 58 | — |
| | No | 43 | F | — | 51 | — |
| | No | 44 | M | — | 66 | — |

In the present study, we provide evidence that: 1) r$(GGGGCC)_{exp}$ adopts both hairpin and G-quadruplex structures—information important for the design of r(GGGGCC)—binding small molecules; 2) human fibroblasts can be directly converted to neurons that recapitulate salient features of disease; 3) small molecules that bind r(GGGGCC)$_{exp}$ inhibit RAN translation and foci formation; and 4) c9RAN proteins are detectable in c9ALS CSF.

Recent studies show that r(GGGGCC) repeats forms G-quadruplexes (Fratta et al., 2012; Reddy et al., 2013), with another reporting they adopt both G-quadruplex and hairpin structures (Haecusler et al., 2014). In agreement with the latter, our chemical and enzymatic probing studies reveal that r(GGGGCC)$_8$ (SEQ ID NO:2) do form a hairpin structure. NMR studies suggest that the hairpin structure predominates at low refolding temperatures while the quadruplex predominates at higher ones. To understand the finer details of this equilibrium in cells, chemical mapping could be completed as described in yeast (Wells et al., 2000), although readout using reverse transcriptase could be challenging. Alternatively, antibodies that recognize RNA quadruplexes could be employed (Lam et al., 2013).

We identified three compounds that bind r(GGGGCC) (1a, 2 and 3), two of which significantly inhibited RAN translation and foci formation in a novel r(GGGGCC)$_{66}$ (SEQ ID NO:1)—expressing cellular model developed for the easy and rapid screening of drugs. In addition, we found that 1a inhibits RAN translation and foci formation in C9ORF72+ iNeurons. To our knowledge, this is the first report showing that adult human fibroblasts can be directly converted to neurons that mirror disease-specific defects, and that these defects can be blocked by pharmacological manipulation. Of interest, RNA foci were observed in both C9ORF72+ fibroblasts and iNeurons, while poly(GP) and poly(PR) inclusions were observed in iNeurons but not fibroblasts. These findings are consistent with our prior observation that poly(GP) inclusions are restricted to neurons in c9FTD/ALS (Ash et al., 2013).

There are at least two potential mechanisms by which our small molecules can affect RAN translation. In the first model, their binding to r(GGGGCC)$_{exp}$ increases the thermodynamic stability of the RNA and is thus an impediment for ribosomal read-through of the transcript. Indeed, 1a and 2 stabilize r(GGGGCC)$_8$ (SEQ ID NO:2) in vitro. In a second model, the binding of small molecules to the repeats impedes initiation of translation at these sites. In a similar fashion, the decrease in foci observed upon treatment could result from the inability of 1a- or 2-bound r(GGGGCC)$_{exp}$ to bind RBPs that promote foci formation.

As a pathological hallmark of c9FTD/ALS, and one that is influenced by r(GGGGCC)$_{exp}$-targeting small molecules, c9RAN proteins have potential to serve as clinically relevant biomarkers. Our discovery that poly(GP) is detectable specifically in c9ALS CSF could facilitate identification of C9ORF72 repeat expansion carriers in the course of standard diagnostic work-ups, and also pave the way in determining whether changes in c9RAN protein levels in CSF correlate with disease severity or progression. Of importance, CSF c9RAN proteins could serve as an enrollment stratification tool in clinical trials, and a pharmacodynamic biomarker to assess efficacy of therapies that target r(GGGGCC)$_{exp}$ (FIG. 4B). While these critical questions are being investigated, it should be kept in mind that the C9ORF72 expansion is bidirectionally transcribed (Gendron et al., 2013; Mori et al., 2013a; Zu et al., 2013); as such, therapeutic approaches may have to target both r(GGGGCC)$_{exp}$ and r(CCCCGG)$_{exp}$. Because poly(GP) proteins are produced by RAN translation of sense and antisense transcripts, poly(GP) immunoassays, such as the one described herein, could be of great use in testing therapeutics toward both r(GGGGCC)$_{exp}$ and r(CCCCGG)$_{exp}$.

EXAMPLES

Materials and Methods

DMS footprinting (Ziehler and Engelke, 2001) and nuclease mapping experiments (Auron et al., 1982) were completed as previously described, as were cloning of r(GGGGCC)$_n$ expression vectors and Western blot analysis (Gendron et al., 2013). For more details on these methods, and for a description of $^1$H NMR spectroscopy, RNA-FISH, conversion of fibroblasts to iNeurons, poly(GP) protein immunoassays, and all other experiments, please see Supplemental Information.

Supplemental Information on Biophysical Studies:

r(GGGGCC)$_8$ (SEQ ID NO:2) Preserves a Hairpin Structure with Periodically Repeating 1×1 Nucleotide GG Internal Loops in Equilibrium with a G-quadruplex With the goal of designing small molecule modulators of r(GGGGCC)$_{exp}$, we investigated the structure of r(GGGGCC)$_{exp}$ by completing spectroscopic, chemical, and enzymatic analyses. First, circular dichroism (CD) studies of r(GGGGCC)$_4$ (SEQ ID NO:7), r(GGGGCC)$_6$ (SEQ ID NO:8) and r(GGGGCC)$_8$ (SEQ ID NO:2) were conducted in the presence of monovalent metal cations (100 mM $K^+$, $Na^+$, or $Li^+$) at pH 7.4. Parallel G-quadruplexes, which are stabilized by $K^+$ and $Na^+$, give a signature negative peak at 242 nm and a large positive peak at 264 nm. Comparison of these CD spectra with r(CGG)$_{12}$, an RNA repeat known to form a hairpin structure (Zumwalt et al., 2007), revealed that both hairpin and quadruplex structures have a positive signal at 264 nm, leaving the negative signal at 242 nm as the only signature to distinguish quadruplexes from hairpins. In the presence of $K^+$, the formation of a negative signal at 242 nm and increased molar ellipticity at 264 nm indicated the potential formation of G-quadruplexes; however, no such effect was observed when r(GGGGCC)$_n$ was studied in the presence of other cations, in particular $Na^+$.

Given that G-quadruplexes have signature melting curves (a large hypochromic transition of UV absorbance at 295 nm (Kumari et al., 2007; Marin and Armitage 2005; Mergny et al., 1998; Mullen et al., 2010)), we probed the structure of r(GGGGCC)$_4$ (SEQ ID NO:7), r(GGGGCC)$_6$ (SEQ ID NO:8), and r(GGGGCC)$_8$ (SEQ ID NO:2) by optical melting in the presence of 100 mM $K^+$ or 100 mM $Na^+$. In the presence of $Na^+$, no hypochromic shift was observed in UV melting profiles at 295 nm for any RNA. Moreover, all three RNAs form intramolecular structures, as their melting temperatures were independent of concentration. In contrast, a hypochromic shift was observed at 295 nm in the presence of $K^+$, but not until above 85° C., indicating the presence of both hairpin and G-quadruplex structures (Table 1).

The folding of r(GGGGCC)$_8$ (SEQ ID NO:2) was next examined using enzymatic and chemical mapping in the presence of $Li^+$ or $K^+$, the latter known to stabilize G-quadruplex formation (Ehresmann et al., 1987; Hardin et al., 1992). Enzymatic mapping was performed using S1 (cleaves single stranded and non-canonically paired nucleotides), T1 (cleaves single stranded and non-canonically paired G's), and V1 (cleaves base pairs). If r(GGGGCC)$_8$ forms a quadruplex, G residues should be protected from cleavage by T1 and S1 (Todd and Neidle, 2011). If r(GGGGCC)$_8$ (SEQ ID NO:2) forms a hairpin structure with internal loops in the stem, an alternating pattern of T1/S1 cleavage and V1 cleavage should be observed. Indeed, our mapping studies revealed such a pattern, suggesting that some population forms a hairpin structure. Enzymatic mapping data were used to construct a model of r(GGGGCC)$_8$'s (SEQ ID NO:2) structure using the program RNAstructure (Mathews et al., 2004), affording a hairpin with GG internal loops. Our hypothesis that r(GGGGCC)$_8$ (SEQ ID NO:2) forms a hairpin was further investigated by chemically probing the RNA's structure by reaction with dimethyl sulfate (DMS). DMS methylates the N7 position of G's (Ehresmann et al., 1987). The N7 position of G's in quadruplexes are hydrogen bonded and thus protected from methylation (Todd and Neidle 2011). In these studies, the majority of guanine N7 positions were susceptible to DMS modification and the pattern did not change in the presence of $Li^+$ or $K^+$.

We additionally explored the structure of r(GGGGCC)$_8$ (SEQ ID NO:2) by analyzing its 1D $^1$H NMR spectra. Guanines in non-canonically paired conformations (internal loops, quadruplexes) typically give rise to imino proton signals from 10 to 12 ppm whereas the resonances from G's in base pairs appear from 12 to 14 ppm (Bugaut et al., 2012). r(GGGGCC)$_8$ (SEQ ID NO:2) prepared in 10 mM Tris HCl and 100 mM KCl was heated at 37° C., 60° C., or 95° C., followed by slow cooling and equilibration at room temperature for 2 h. Well defined peaks were observed in two regions (10.0-11.8 and 12.0-13.5 ppm) after annealing at 37° C., suggesting formation of a hairpin structure with non-canonically paired Gs. As the annealing temperature increased, however, the peaks in both regions became broad. The signals in the 12-14 ppm range (Watson-Crick paired Gs) were reduced while those in the 10-12 ppm range were increased, indicating increased population of a G-quadruplex. The existence of both conformations is not surprising, as other studies have suggested RNAs that form quadruplexes can form alternative structures that include hairpins (Bugaut et al., 2012; Fojtik et al., 2004).

Supplemental Experimental Procedures

List of Abbreviations

ATP, adenosine triphosphate; BLI, biolayer interferometry; bp, base pair; BSA, bovine serum albumin; CA, chlorambucil; CD, circular dichroism; DCM, dichloromethane; DIPEA, N,N-diisopropylethylamine; DMF, N,N-dimethylformamide; DMS, dimethyl sulfate; DMSO, dimethyl sulfoxide; DNA, deoxyribonucleic acid; DEPC-PBS, DEPC-treated PBS; DPBS, Dulbecco's phosphate buffered saline; EDTA, ethylenediaminetetraacetic acid; EtOAC, ethyl acetate; FBS, fetal bovine serum; HBTU, O-(benzotriazol-1-yl)-N,N,N',N'-tetramethyluronium hexafluorophosphate; HEPES, 4-(2-hydroxyethyl)piperazine-1-ethanesulfonic acid; HOBt, 1-hydroxybenzotriazole; HPLC, high performance liquid chromatography; HRMS, high resolution mass spectrometry; LC-MS, liquid chromatography-mass spectrometry; MALDI-TOF, matrix-assisted laser desorption/ionization time-of-flight; MS, mass spectrometry; NaOAc, sodium acetate; NMR, nuclear magnetic resonance; PAGE, polyacrylamide gel electrophoresis; PBS, phosphate buffered saline; PMSF, phenylmethylsulfonyl fluoride; qRT-PCR, quantitative real time polymerase chain reaction; RNA, ribonucleic acid; SDS, sodium dodecyl sulphate; $t_R$, retention time; TBE, Tris/Borate/EDTA; TBST, Tris buffered saline supplemented with 0.05% Tween-20; TFA, trifluoroacetic acid; Tris, tris(hydroxymethyl)aminomethane; UV, ultraviolet Reagents and oligonucleotide preparation. All reagents used for chemical synthesis were purchased from commercially available sources and used without further purification unless noted otherwise. NMR solvents were obtained from Cambridge Isotope Labs and used as is. RNA oligonucleotides (Dharmacon) were deprotected per the manufacturer's recommended protocol and desalted using a PD-10 gel filtration column (GE Healthcare). Concentrations were determined by measuring absorbance at 260 nm using a Beckman Coulter DU800 UV-Vis spectrophotometer equipped with a Peltier temperature controller unit. Extinction coefficients (at 260 nm) were calculated using the HyTher server (Peyret et al., 1999; SantaLucia, 1998), which is based on nearest neighbour parameters (Puglisi and Tinoco, 1989). RNA oligonucleotides were radioactively labelled at the 5' end using T4 polynucleotide kinase (New England Biolabs) and [γ-$^{32}$P] ATP (PerkinElmer) and purified by either passing through a Sephadex G-25 column (Promega) or by PAGE as previously described (Disney et al., 2000). DNA oligonucleotides (Integrated DNA Technologies, Inc. (IDT)) were used without further purification.

Instrumentation. Mass spectra were collected using an ABI 4800 MALDI-TOF or Varian 500-MS IT mass spectrometer. Reverse-phase HPLC was completed using a Waters 1525 binary HPLC pump equipped with a Waters 2487 dual absorbance detector system. Optical melting spectra were acquired using a Beckman Coulter DU800 UV-Vis spectrometer connected to a Peltier heater. Circular dichroism experiments were performed on a Jasco J-815 spectrometer equipped with a Jasco Peltier temperature controller. TO-PRO-1 displacement assays were performed on a PerkinElmer Envision® multilabel reader. Gel images were acquired using a Molecular Dynamics Typhoon 9410 variable mode imager. BLI experiments were performed on ForteBio Octet RED. The concentration of total RNA isolated from cells was determined using a Thermo Scientific Nanodrop 2000C spectrophotometer. qRT-PCR analyses were performed on an ABI 7900 HT Real-Time PCR System. $^1$H NMR spectra of RNA were recorded at 10° C. using a 700 MHz Bruker Avance TCI spectrometer equipped with a cryogenic TCI ATM probe, water suppression was achieved using excitation sculpting. $^1$H NMR (400 MHz) and $^{13}$C NMR (100 MHz) spectra for compound characterization were recorded at 25° C. on a 400 MHz Bruker Avance spectrometer. Chemical shifts (δ) are given in ppm relative to tetramethylsilane or the respective NMR solvent; coupling constants (J) are in Hertz (Hz). Abbreviations used are s, singlet; bs, broad singlet; d, doublet; dd, doublet of doublets; t, triplet; dt, doublet of triplets; td, triplet of doublets; tt, triplet of triplets; bt, broad triplet; q, quartet; m, multiplet; and bm, broad multiplet. HRMS were obtained at the Scripps Florida Mass Spectrometry and Proteomics Laboratory.

Circular Dichroism (CD). RNA samples (4 μM) were folded in 1× CD Buffer (10 mM Tris HCl, pH 7.4 containing no monovalent cation or 100 mM LiCl, NaCl or KCl) by heating at 95° C. for 5 min and then slowly cooling to room temperature. Samples were then transferred into a 1 mL quartz cell with a pathlength of 1 mm. CD spectra were recorded at 20° C. by measuring ellipticity from 220 to 320 nm at a rate of 50 nm/min, a 2 second digital integration time (D.I.T.), 1 nm data pitch, and 1 nm band width. The background was subtracted from each spectrum, which were smoothed and normalized to zero at the starting point (320 nm).

Nuclease Mapping. Nuclease mapping experiments were performed as previously described (Auron et al., 1982). Briefly, 5' end-$^{32}$P-labeled r(GGGGCC)$_8$ (SEQ ID NO:2) was dissolved in 1× Mapping Buffer (10 mM Tris HCl, pH 7.4, 0.3 mM $MgCl_2$) supplemented with 185 mM KCl. In the case of Si footprinting, the buffer was also supplemented with 10 mM $ZnCl_2$. The RNA was folded by heating in the corresponding buffer to 95° C. for 5 min and slowly cooling to room temperature on the bench top.

Enzymatic digestions using T1 (0.01 U/μL) under denaturing conditions (1× RNA Sequencing Buffer; Life Technologies), T1 (1 U/μL), V1 (0.001 U/μL) and S1 (0.1 U/μL) under non-denaturing condition were carried out at room temperature for 15 min and quenched by the addition of 1× Loading Buffer (1 mM Tris HCl, pH 7.5, 10 mM EDTA, and 4 M urea) and incubation at 95° C. for 2 min. Cleavage products were separated on a denaturing 20% polyacrylamide gel and visualized by autoradiography. Sites of cleavage were used as restraints in secondary structure prediction by free energy minimization (RNAstructure, version 5.4) (Bellaousov et al., 2013).

DMS Footprinting. DMS footprinting experiments were completed as previously described Ziehler and Engelke, 2001). Briefly, 5' end-$^{32}$P-labeled $r(GGGGCC)_8$ (SEQ ID NO:2) was folded in 10 mM Tris HCl, pH 7.4, containing 185 mM KCl, NaCl, or LiCl by heating at 95° C. and slowly cooling to room temperature. To the samples were added DMS (dissolved in 1:1 $EtOH:H_2O$) to a final concentration of 3% (v/v), and the samples were incubated for 2 min. Reactions were quenched by ethanol precipitation; the resulting pellets were washed once with 70% ethanol and briefly dried in a vacuum concentrator. The RNA samples were dissolved in 1 M Tris HCl, pH 8 followed by addition of 0.1 M $NaBH_4$ and incubation on ice for 30 min in the dark. The reactions were quenched by ethanol precipitation as described above. Aniline cleavage of the modified RNA was completed by dissolving the RNA in freshly prepared 1 M aniline in 0.3 M NaOAc, pH 4.5 followed by incubation at 60° C. for 20 min. The samples were ethanol precipitated and dissolved in 1× Loading Buffer. Fragments were separated on a denaturing 20% polyacrylamide gel and visualized by autoradiography.

Optical Melting. The RNA of interest (1-35 μM) was folded in 10 mM Tris HCl, pH 7.4 and 100 mM NaCl or 100 mM KCl by heating at 95° C. for 5 min and slowly cooled to room temperature. For experiments completed for $r(GGGGCC)_8$ (SEQ ID NO:2) in the presence of small molecule, 1 μM RNA was folded as described above followed by addition of 3 μM compound and incubation at room temperature for 15 min. Absorbance versus temperature spectra were then acquired at 260 nm and 295 nm at a rate of 1° C./min. Melting curves were fit to a self-complementary model using MeltWin (http://www-.meltwin.com). The program fits each curve and calculates thermodynamic parameters and melting temperature ($T_m$) (see Table 1, Table 3, FIG. 1C).

$^1$H NMR spectroscopy. A 600 μM sample of $r(GGGGCC)_8$ (SEQ ID NO:2) was prepared in 10 mM Tris HCl, pH 7.4 and 100 mM KCl and annealed at the appropriate temperature for 5 min. The sample was then slowly cooled to room temperature. After equilibration at room temperature for 2 h, the sample was transferred to a 3 mm Shigemi $D_2O$ NMR tube, and NMR spectra were recorded at 10° C.

TO-PRO-1 displacement screening. $r(GGGGCC)_8$ (SEQ ID NO:2) (36 nM) was folded in 8 mM $Na_2HPO_4$, pH 7.0, 185 mM NaCl, and 1 mM EDTA by heating at 95° C. for 5 min and slowly cooling to room temperature. TO-PRO-1 and BSA were then added to final concentrations of 10 nM and 40 μg/mL, respectively, and the samples were incubated at room temperature for 15 min. The compound of interest (100 μM) was added, and the samples were incubated for an additional 15 min at room temperature. After incubation, fluorescence intensity was recorded and converted to the percentage of dye-RNA complex using equation 1:

$$y = \frac{I - I_0}{I_{max} - I_0} \times 100\% \quad \text{(eq. 1)}$$

where I is the observed fluorescence intensity, $I_0$ is the fluorescence intensity in the absence of RNA, $I_{max}$ is the fluorescence intensity in the absence of compound.

Figure 1A:
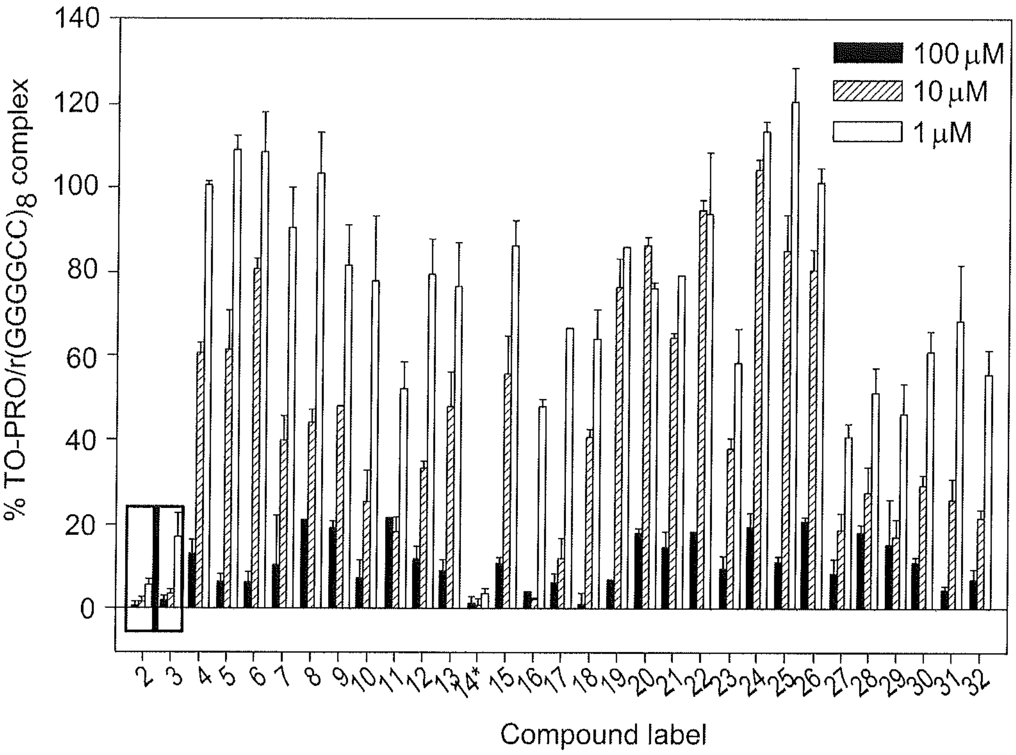
FIG. 1A) Screening for lead compounds that bind $r(GGGGCC)_8$ (SEQ ID NO:2) using a dye (TO-PRO-1) displacement assay. An initial screen completed with 100 μM compound identified 31 potential leads (from 132 total compounds) that were further refined by screening at 10 and 1 μM concentrations. Lead compounds are highlighted in red rectangles. Data are presented as mean±SD (n=3). * Compound is unstable as determined by LC-MS.
Figure 1C:
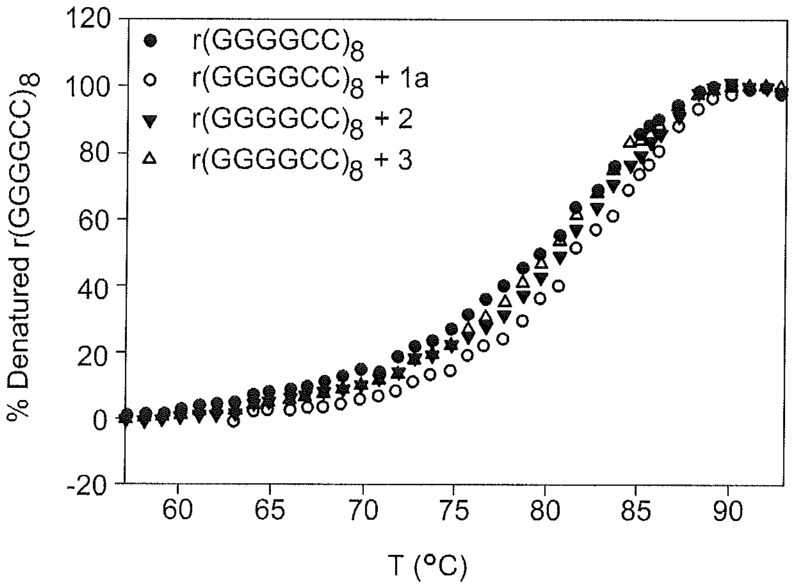
FIG. 1C) Optical melting experiment of r(GGGGCC)$_8$ (SEQ ID NO:2) with 1a, 2, and 3. Treatment of r(GGGGCC)$_8$ (SEQ ID NO:2) with compound 1a and 2 (1:3) stabilizes the RNA repeat and increases its melting temperature.
Figure 1B:
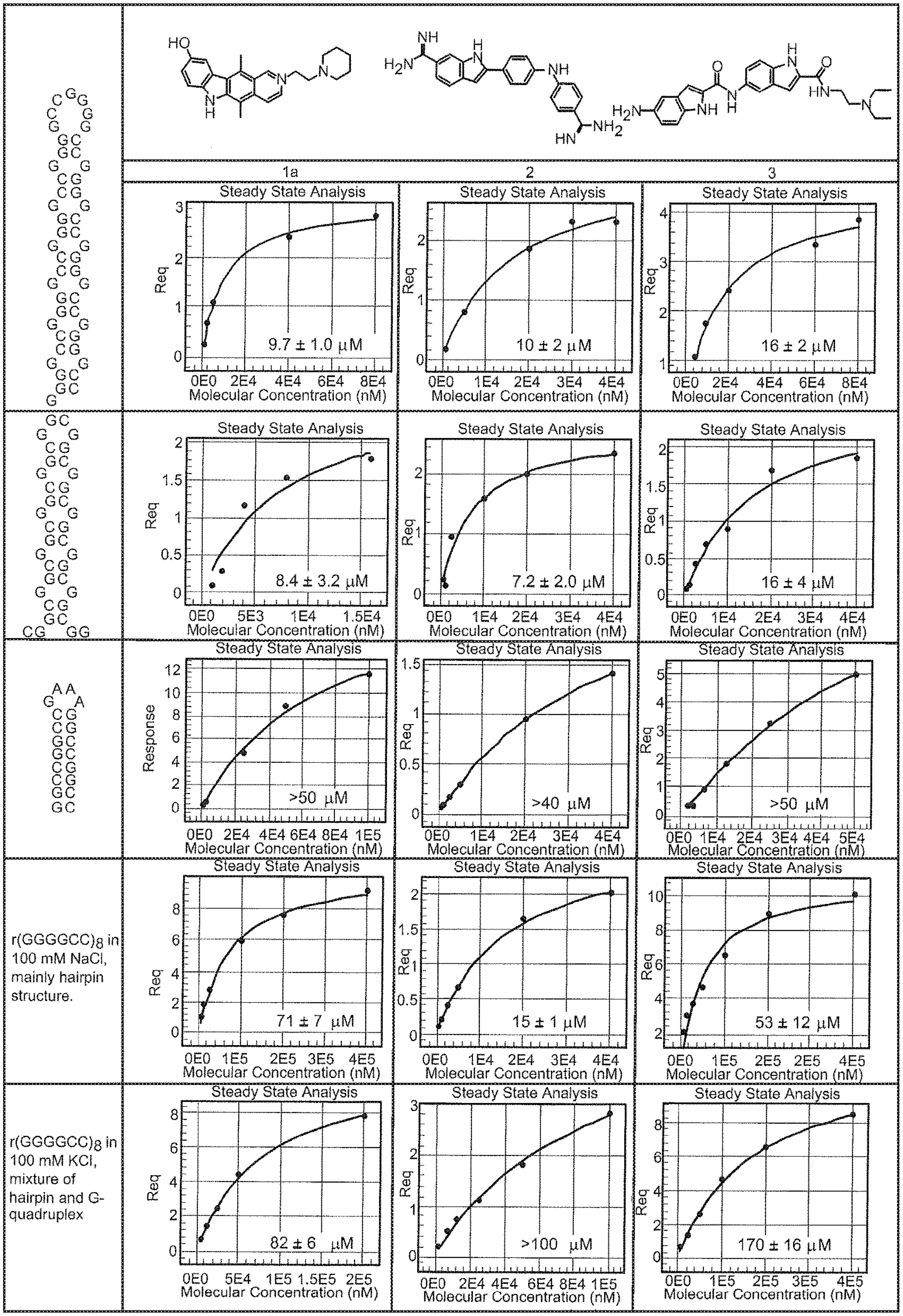
FIG. 1B) Binding affinity of lead compounds 1a, 2, and 3 to $r(CGG)_{12}$ (SEQ ID NO:3), r(GGCC)$_4$ (SEQ ID NO:4), and hairpin and G-quadruplex conformations of r(GGGGCC)$_8$ (SEQ ID NO:2), as determined by BLI.

This screen identified 31 compounds (out of 132) that displaced >95% of TO-PRO-1 from the RNA, which were carried forward to additional screening at lower concentrations (10 and 1 μM) (see FIG. 1A, Table 2). As a control, the fluorescence of hit compounds in the presence of TO-PRO-1 but in the absence of $r(GGGGCC)_8$ (SEQ ID NO:2) was also measured.

Biolayer Interferometry (BLI). BLI was used to measure the binding affinities of 1a, 2, and 3 for three different RNAs, including 5'-Biotin-$r(GGGGCC)_8$ (SEQ ID NO:2), 5'-Biotin-$r(CGG)_{12}$ (SEQ ID NO:3), and a hairpin containing all GC pairs in the stem and a GAAA tetraloop (see FIG. 1B). The appropriate 5'-biotinylated RNA (100 nM) was folded in 1× Kinetics Buffer (ForteBio; 1× PBS, 0.1% (w/v) BSA, 0.02% (v/v) Tween20, and 0.05% (w/v) sodium azide) supplemented with no cation, 100 mM NaCl, or 100 mM KCl by heating at 95° C. for 5 min and slowly cooling to room temperature. The RNA (200 μL aliquots) was then added to a black 96-well plate (Greiner Bio-One). The compound of interest (16-100 μM; 200 μL aliquots; 2-fold serial dilutions; 7 samples total) was dissolved in 1× Kinetics Buffer. A sample with no compound was used as background. All experiments were performed at 30° C. with agitation set to 1000 rpm.

The biotinylated RNA (ligand) was loaded onto the surface of streptavidin biosensors (SA) for 660 s. Optimal response levels were between 0.5 and 2 nm, and variability within a row of eight tips did not exceed 0.2 nm. Biosensors were then washed in 1× Kinetics Buffer for 300 s followed by association of the compound (analyte) for 5000 s. Finally, dissociation of the ligand-analyte interaction was analyzed for 5000 s. The resulting curves were corrected by subtracting the response recorded on a sensor loaded with ligand (RNA) but incubated with no analyte (compound). Data analyses and curve fitting were completed using Octet Data Analysis, version 7.0. Experimental data were fitted using the 2:1 heterogeneous ligand (HL) curve fit. Global analysis of all data sets acquired for different analyte concentrations, assuming reversible binding, was completed using nonlinear least squares fitting. $K_{ds}$ were calculated using steady-state kinetic analysis of the estimated response at equilibrium ($Re_q$) according to equation 2 and 3 (see FIG. 1B).

$$y = R_{max} \frac{[\text{Analyte}]}{[\text{Analyte}] + K_d} \quad \text{(eq. 2)}$$

$$R_{max} = R_{eq} \frac{k_{on} \times [\text{Analyte}]}{k_{on} \times [\text{Analyte}] + k_{off}} \quad \text{(eq. 3)}$$

where [Analyte] is the concentration of compound, $R_{eq}$ is the estimated response at equilibrium, $k_{on}$ is association constant, $k_{off}$ is dissociation constant.

Synthesis of 1a-CA-biotin

2-(5-(aminopentyl)-9-hydroxy-5,11-dimethyl-6H-pyrido[4,3-b]carbazol-2-ium

A sample of 9-hydroxyellipticine (Deane et al., 2011; Plug et al., 1992) (50 mg, 0.19 mmoles) was dissolved in 4 mL of DMF, and tert-butyl (5-bromopentyl)carbamate (Hingorani et al., 2013) (130 mg, 0.49 mmoles in 2 mL of DMF) was added. The mixture was stirred at room temperature overnight. After removing DMF in vacuo, TFA dissolved in DCM was added to the residue, and the mixture was stirred at room temperature for 1 h. The mixture was concentrated, and the product was purified by HPLC (20-60% MeOH/$H_2O$ with 0.1% TFA over 60 min) to yield the desired product as a red solid (22 mg, 33% yield). $^1H$ NMR (400 MHz, $CD_3OD$) δ 9.51 (s, 1H), 8.15 (d, J=7.2 Hz, 1H), 8.05 (d, J=7.2 Hz, 1H), 7.27 (d, J=2.2 Hz, 1H), 7.14 (d, J=8.6 Hz, 1H), 6.89 (dd, J=8.6 Hz, J=2.3 Hz 1H), 4.63 (t, J=7.6 Hz, 2Hs), 3.00 (t, J=7.4 Hz, 2Hs), 2.90 (s, 3Hs), 2.58 (s, 3Hs), 2.13 (m, 2Hs), 1.81 (m, 2Hs), 1.58 (m, 2Hs). $^{13}C$ NMR (400 MHz, $CD_3OD$) δ 153.0, 146.2, 146.0, 137.4, 134.1, 133.6, 130.9, 127.3, 124.0, 121.3, 121.2, 118.1, 112.7, 110.9, 110.3, 61.1, 40.4, 31.9, 28.1, 24.4, 15.0, 11.9. HRMS (FAB) calculated for $C_{22}H_{26}N_3O$ ($M^+$) 348.2070, found 348.2073.

2-(5-(2-((((9H-fluoren-9-yl)methoxy)carbonyl) amino)-6-((tert-butoxycarbonyl)amino) hexanamido) pentyl)-9-hydroxy-5,11-dimethyl-6H-pyrido[4,3-b] carbazol-2-ium Fmoc-Lys(Boc)-OH (54 mg, 0.11 mmoles), HBTU (130 mg, 0.34 mmoles), HOBT (52 mg, 0.34 mmoles), and DIPEA (88 mg, 0.68 mmoles) were dissolved in 1 mL DMF, and the mixture was stirred at room temperature for 30 min. Then, 2-(5-(aminopentyl)-9-hydroxy-5,11-dimethyl-6H-pyrido[4,3-b]carbazol-2-ium (20 mg, 0.057 mmoles) was added to the mixture, which was stirred at room temperature overnight. EtOAc was added to the solution, and the organic layer was washed with $H_2O$ and dried over $Na_2SO_4$. The concentrated residue was filtered by silica gel column and was used for the next reaction without further purification.

2-(5-(6-amino-2-(5-(2-oxohexahydro-1H-thieno[3,4-d]imidazol-4-yl)pentanamido) hexanamido)pentyl)-9-hydroxy-5,11-dimethyl-6H-pyrido[4,3-b]carbazol-2-ium A solution of 2-(5-(2-((((9H-fluoren-9-yl)methoxy)carbonyl)amino)-6-((tert-butoxycarbonyl)amino) hexanamido) pentyl)-9-hydroxy-5,11-dimethyl-6H-pyrido[4,3-b]carbazol-2-ium from the previous synthetic step was dissolved in 5 mL 20% piperidine/DMF and stirred at room temperature for 2 h, and the solvent was removed in vacuo. A mixture of biotin (98 mg, 0.40 mmoles), HBTU (303 mg, 0.80 mmoles), HOBT (122 mg, 0.80 mmoles), and DIPEA (206 mg, 1.6 mmoles) in 2 mL DMF was stirred for 30 min at room temperature. The mixture was then added to the concentrated residue and stirred at room temperature overnight. The solution was concentrated and treated with 10 mL 50% TFA in DCM for 2 h. After removing the solvent, the product was dissolved in 20% MeOH in $H_2O$ and purified by HPLC (20-75% MeOH/$H_2O$ with 0.1% TFA over 60 min) to yield the desired product as an orange solid (11 mg, 28% yield). $^1H$ NMR (400 MHz, $CD_3OD$) δ 9.74 (s, 1H), 8.28 (s, 2Hs), 7.63 (d, J=2.2 Hz, 1H), 7.38 (d, J=8.6 Hz, 1H), 7.10 (dd, J=8.6 Hz, J=2.3 Hz 1H), 4.67 (t, J=7.4 Hz, 2Hs), 4.50 (dd, J=7.8 Hz, J=4.5 Hz 1H), 4.29 (dd, J=7.8 Hz, J=4.4 Hz 1H), 4.23 (dd, J=9.0 Hz, J=5.3 Hz 1H), 3.28 (m, 2Hs), 3.16 (s, 3Hs), 3.15 (m, 2Hs), 2.91 (m, 3Hs), 2.77 (s, 3Hs), 2.71 (d, J=12.8 Hz, 1H), 2.26 (t, J=7.1 Hz, 2Hs), 2.13 (m, 2Hs), 1.60 (m, 10Hs), 1.47 (m, 4Hs), 1.39 (m, 4Hs). $^{13}C$ NMR (400 MHz, $CD_3OD$) δ 174.8, 173.0, 164.8, 159.6, 151.9, 145.1, 136.4, 133.2, 132.5, 126.5, 123.0, 120.1, 117.0, 111.5, 109.8, 109.3, 61.9, 60.2, 60.0, 55.7, 53.5, 39.6, 39.1, 38.4, 34.8, 30.9, 30.6, 29.3, 28.4, 28.0, 26.7, 25.3, 23.1, 22.8, 13.8, 10.6. HRMS (FAB) calculated for $C_{38}H_{52}N_7O_4S$ ($M^+$) 702.3796, found 702.3802.

2-(5-(6-(4-(4-(bis(2-chloroethyl)amino)phenyl)butanamido)-2-(5-(2-oxohexahydro-1H-thieno[3,4-d] imidazol-4-yl)pentanamido)hexanamido)pentyl)-9-hydroxy-5,11-dimethyl-6H-pyrido[4,3-b]carbazol-2-ium Chlorambucil (26 mg, 0.085 mmoles), HBTU (43 mg, 0.11 mmoles), HOBT (17 mg, 0.11 mmoles) and DIPEA (58 mg, 0.44 mmoles) in 1 mL DMF were stirred at room temperature for 40 min. Into the mixture was added 2-(5-(6-amino-2-(5-(2-oxohexahydro-1H-thieno[3,4-d]imidazol-4-yl)pentanamido)hexanamido)pentyl)-9-hydroxy-5,11-dimethyl-6H-pyrido[4,3-b]carbazol-2-ium (11 mg, 0.016 mmoles). The solution was stirred at room temperature overnight and concentrated in vacuo. After removing the solvent, the product was dissolved in 20% acetonitrile in $H_2O$ and purified by HPLC (20-75% acetonitrile/$H_2O$ with 0.1% TFA for 60 min) to yield the desired product as a yellow solid (2.1 mg, 15% yield). HRMS (FAB) calculated for $C_{52}H_{69}Cl_2N_8O_5S$ ($M^+$) 987.4483, found 987.4488; $t_R$=29 min.

Cloning of r(GGGGCC)$_n$ expression vectors. The generation of r(GGGGCC)$_2$, r(GGGGCC)$_{20}$ and r(GGGGCC)$_{66}$ (SEQ ID NO:1) expression vectors was previously reported (Gendron et al, 2013). In brief, genomic DNA from muscle or spleen from a C9ORF72 expanded repeat carrier was used as a template in a nested PCR strategy using ThermalAce DNA Polymerase (Invitrogen) to amplify the (GGGGCC)$_n$ repeat region, including 113 bp of 5' and 99 bp of 3' flanking sequence. The PCR products were cloned into the pAG3 expression vector. These constructs contain 3 upstream stop codons in each reading frame. Clones containing r(GGGGCC)$_2$ (SEQ ID NO:9), r(GGGGCC)$_{20}$ (SEQ ID NO:10) and r(GGGGCC)$_{66}$ (SEQ ID NO:1) were verified by hairpin sequence analysis.

Identification of the RNA targets of 1a, 2 and 3 by qRT-PCR. COS7 cells were grown as monolayers in a 75 $cm^2$ flask to ~95% confluency and then transfected with r(GGGGCC)$_{66}$ (SEQ ID NO:1) using Lipofectamine 2000 (Invitrogen) per the manufacturer's recommended protocol. Approximately 16 h post-transfection, 1a-CA-Biotin and the compound of interest, or vehicle, were added to the cells, and the samples were incubated at 37° C. for 20-24 h. Total RNA was extracted using Trizol reagent (Ambion) according to the manufacturer's protocol. Approximately 100 μg of isolated total RNA in 100 μl of 1× PBS was added to a 2 ml centrifuge tube containing a filter column (Sigma-Aldrich) with 300 μl of streptavidin beads (Sigma-Aldrich; washed three times with 300 μl of 1× PBS). The RNA and beads were incubated at room temperature for 1 h with gentle agitation (700 rpm). The solution containing unbound RNA was removed by filtration, and the beads were washed with 1× TBST (6×200 μl) until RNA was no longer eluted as determined by absorbance at 260 and 280 nm. Bound RNA-1a-CA-Biotin adducts were released from beads by heating in 50 μl 1× Elution Buffer (95% formamide, 10 mM EDTA, pH 8.2) at 65° C. for 5 min. The concentration of the bound RNA was quantified by UV absorbance. cDNA was generated from 50 ng of RNA using a qScript cDNA Synthesis Kit (Quanta Biosciences) per the manufacturer's protocol. Power SYBR® Green PCR Master Mix (Applied Biosystems) was used to quantify the amount of r(GGGGCC)$_{66}$ (SEQ ID NO:1) according to the manufacturer's protocol. The amount of the r(GGGGCC)$_{66}$ (SEQ ID NO:1) was normalized relative to 18S rRNA. Primer sequences for r(GGGGCC)$_{66}$ (SEQ ID NO:1) (C9down-F and C9down-R), 18S rRNA (18S-F and 18S-R), and β-actin internal control (hACTB-F and hACTB-R) are provided in Table 5.

TABLE 5

Sequences of primers used in qRT-PCR analysis.[a]

| Primer ID | Sequence |
|---|---|
| C9down-F | 5'-GGG CCC TAT TCT ATA GTG TCA CC (SEQ ID NO: 13) |
| C9down-R | 5'-ACA ACA GAT GGC TGG CAA C (SEQ ID NO: 14) |
| 18S-F | 5'-GTA ACC CGT TGA ACC CCA TT (SEQ ID NO: 15) |
| 18S-R | 5'-CCA TCC AAT CGG TAG TAG CG (SEQ ID NO: 16) |
| hACTB-F | 5'-CCT GGC ACC CAG CAC AAT (SEQ ID NO: 17) |
| hACTB-R | 5'-GGG CCG GAC TCG TCA TAC (SEQ ID NO: 18) |

[a]"F" and "R" indicates forward and reverse primers, respectively.

Western blot analysis of c9RAN proteins. HEK293 cells were cultured in Opti-Mem supplemented with 10% FBS and 1% penicillin/streptomycin. To detect products of r(GGGGCC)$_n$ RAN translation, 90% confluent cells grown in 6-well plates were transfected with 5 μg of (GGGGCC)$_2$, (GGGGCC)$_{20}$ or (GGGGCC)$_{66}$ vectors using Lipofectamine 2000 (Invitrogen) according to the manufacturer's instructions. Twenty-four hours later, cell pellets were collected. To determine the effect of compounds on RAN translation, cells were treated with DMSO (vehicle) or compound (1a, 2 or 3) 4 h after transfection, followed by collection of cell pellets 24 h later. Western blotting was performed as previously described (Gendron et al., 2013). In brief, cell pellets were lysed in Co-IP buffer (50 mm Tris-HCl, pH 7.4, 300 mM NaCl, 1% Triton-X-100, 5 mM EDTA, 2% sodium dodecyl sulfate (SDS), plus phenylmethylsulfonyl fluoride (PMSF) and both a protease and phosphatase inhibitor mixture). After centrifugation at 16,000×g for 20 min at 4° C., the supernatant was collected and protein concentration determined by BCA assay. Samples were prepared in Laemmli's buffer, heated for 5 min at 95° C., and equal amounts of protein were loaded into Novex® 4-20% Tris-Glycine gels (Invitrogen). After transfer, blots were blocked with 5% non-fat dry milk in Tris-buffered saline +0.1% Triton X-100 (TBST) for 1 h, and then incubated with rabbit polyclonal anti-GP, anti-GA or anti-GR (1:1,000) overnight at 4° C. Anti-GAPDH (1:10,000, BioDesign) was used to ensure equal loading among wells. Membranes were washed three times for 10 min in TBST and incubated with donkey anti-rabbit or anti-mouse IgG conjugated to horseradish peroxidase (1:5000; Jackson ImmunoResearch) for 1 h. Protein expression was visualized by enhanced chemiluminescence treatment and exposure to film.

Immunoassay analysis of c9RAN proteins. As an alternative means to measure poly(GP) proteins, Meso Scale Discovery (MSD) electrochemiluminescence detection technology was utilized to establish sandwich immunoassays using polyclonal anti-GP as capture and detection antibodies. For validation of poly(GP) assay specificity, synthetic peptides (200 ng/ml) representing each possible protein RAN translated from the sense or antisense transcripts of the expanded C9ORF72 repeat [(GA)$_8$ (SEQ ID NO:19), (GR)$_8$ (SEQ ID NO:20), (GP)$_8$ (SEQ ID NO:6), (PA)$_8$ (SEQ ID NO:21), (PR)$_8$ (SEQ ID NO:22)] were assayed (FIG. 4A). Poly(GP) proteins were also measured in lysates from cultured cells (10-35 μg of protein per well) prepare as described above, or from RIPA-soluble homogenates from frozen frontal cortical tissues (35 μg of protein per well). Brain homogenates were prepared as previously described (Almeida et al., 2013). In brief, tissue was lysed in cold RIPA buffer and sonicated on ice. Lysates were cleared by centrifugation at 100,000 g for 30 min at 4° C. The supernatant was collected and protein concentration was determined by BCA assay. Poly(GP) protein expression was similarly evaluated in CSF (90 μl per well, in duplicate or triplicate wells) from 5 healthy controls, 25 ALS patients without the C9ORF72 repeat expansion, and 14 ALS patients with the expansion (see Table 4 for patient information and the section on Human Samples below for additional information on CSF collection).

A second MSD sandwich immunoassay was developed for the detection of poly(PR) proteins using polyclonal anti-PR as capture and detection antibodies. To validate specificity of the poly(PR) assay, lysates from cells transfected to express each possible protein RAN translated from the sense or antisense transcripts of the expanded C9ORF72 repeat [GFP-(GA)$_5$, GFP-(GR)$_5$, GFP-(GP)$_5$, GFP-(PA)$_5$, GFP-(PR)$_5$] were assayed, as were lysates from cells expressing (CCCCGG)$_{66}$ (FIG. 2F).

RNA fluorescence in situ hybridization (FISH) of (GGGGCC)$_n$-expressing cells. HEK293T cells grown on glass coverslips in 24-well plates were transfected with 0.5 μg r(GGGGCC)$_2$, r(GGGGCC)$_{20}$ or r(GGGGCC)$_{66}$ vectors. After 24 h, cells were fixed in 4% paraformaldehyde for 20 min, permeabilized in ice-cold methanol for 10 min, and washed 3 times with DEPC-treated PBS (DEPC-PBS). Cells were hybridized with denatured Cy3-conjugated (GGCCCC)$_4$ probe (2 ng/μl) in hybridization buffer (50% formamide, 10% dextran sulfate, 0.1 mg/mL yeast tRNA, 2×SSC, 50 mM sodium phosphate) overnight at 37° C. Cells were then washed once with 40% formamide/1×SSC for 30 min at 37° C. and twice with DEPC-PBS at room temperature for 5 min, followed by counterstaining with Hoechst 33258 (1 μg/ml, Invitrogen). Immunostained cells were visualized using a Zeiss Axiovert Fluorescence Microscope with apotome module. To evaluate the effect of compounds on foci formation, HEK293 cells grown on glass coverslips in 24-well plates were transfected with 0.6 μg of $r(GGGGCC)_{66}$ vector. Four hours after transfection, cells were treated with DMSO or compound (1a, 2 or 3) for 24 h, and then subjected to FISH as described above. To quantify foci-bearing cells, coverslips mounted on slides were scanned by Aperio ScanScope. Ten fields were randomly selected under 20× magnification. For each field, the number of foci-positive nuclei and the total number of nuclei were counted using MetaMorph software. These counts were used to determine the average percentage of foci-positive cells for each condition.

To determine whether r(GGGGCC)-binding compounds impair binding of the RNA-probe to r(GGGGCC), non-treated $(GGGGCC)_{66}$-expressing cells were fixed with 4% PFA, permeabilized with 0.2% Triton X-100 in DEPC-PBS, and washed twice with DEPC-PBS. RNA FISH was then performed using hybridization buffer containing the Cy3-$(GGGGCC)_4$ RNA probe and either DMSO or 1a in excess of 20 times the molar concentration of the probe.

Western blot analysis and RNA-FISH of cells expressing antisense repeats. To examine the effect of 1a on RAN translation and foci formation in cells expressing antisense (CCCCGG) repeats, we utilized a previously described $(CCCCGG)_{66}$ expression vector (Gendron et al., 2013). Transfection, treatment, Western blotting, and RNA-FISH using a 5'Cy3-$(GGGGCC)_4$-3' probe from IDT, were conducted as described above for $(GGGGCC)_{66}$-expressing cells.

Western blot analysis of RAN translation in a FXTAS cell model. Studies were completed using a plasmid in which $r(CGG)_{88}$ is embedded in the 5' UTR of an open reading frame encoding GFP (Todd et al., 2013). Therefore, RAN products are fused to GFP and can be detected using an anti-GFP antibody (Todd et al., 2013). COS7 cells were grown as monolayers in 96-well plates in growth medium (1× DMEM, 10% FBS, and 1× GlutaMax (Invitrogen)). After the cells reached 90-95% confluency, they were transfected with 200 ng of plasmid using Lipofectamine 2000 (Invitrogen) per the manufacturer's standard protocol. Compound 1a was added to the transfection cocktail, which was then applied to the cells. The transfection cocktail was replaced with growth medium containing 1a approximately 5 h post transfection, and the cells were incubated at 37° C. for 18 h. Cells were lysed in the plate using 100 μl/well of MPER Mammalian Protein Extraction Reagent (Pierce Biotechnology) containing 1 μl of Halt Protease Inhibitor cocktail (Thermo Scientific). Cellular proteins were separated by SDS-PAGE (10% polyacrylamide) and then transferred to a PVDF membrane by wet transfer method. Protein content was analyzed by Western blotting by using anti-GFP (Santa Cruz) or anti-β-actin (Sigma Aldrich) as primary antibodies and anti-IgG-horseradish peroxidase conjugate as the secondary antibody. Chemiluminescent signal was generated by SuperSignal West Pico Chemiluminescent substrate (Thermo Scientific), and the blot was imaged with X-ray film (Phenix Research).

Human Samples. Frozen frontal cortex tissue used for biochemical analysis included samples from 6 FTD/ALS cases with the C9ORF72 expansion, and 4 FTD/ALS cases without the expansion.

Fibroblasts were derived from skin sampled by punch biopsy on the anterior aspect of the forearm. Skin biopsies were obtained from six individuals, which included three control participants (control 1: female diagnosed with sixth nerve palsy, 61 years of age at the time of biopsy; control 2: healthy female, 64 years of age at the time of biopsy; control 3: healthy female, 38 years of age at the time of biopsy) and three repeat expansion carriers (carrier 1: 28 year old female at the time of biopsy; carrier 2: female diagnosed with ALS at 49 years of age, 50 years of age at the time of biopsy; carrier 3: male diagnosed with ALS/FTD at 41 years of age, 43 years of age at the time of biopsy). Fibroblasts were generated by ReGen Theranostics Inc (Rochester, Minn.).

CSF was obtained from healthy controls or ALS patients seen at the ALS Center at Mayo Clinic Florida, the National Institutes of Health (NIH), the IRCCS Istituto Auxologico Italiano (Milan, Italy), the University of Massachusetts Medical School, and Massachusetts General Hospital (Table 4). CSF was collected via standard lumbar puncture, aliquoted and stored at −80° C. ALS patients had El Escorial clinically definite, probable, laboratory supported probable or possible ALS of <5 years' duration. Patients received lumbar puncture generally in the diagnostic early phase of the disease. Patients receiving tracheostomy ventilation or non-invasive mechanical ventilation for >23 h/day were excluded. Also excluded were patients with a history of conditions which could potentially alter the blood-CSF barrier (i.e., spinal surgery). The presence or absence of the C9ORF7 2 repeat expansion was determined by repeat-primed polymerase chain reaction (PCR) method as previously described (DeJesus-Hernandez et al., 2011) supported by amplicon-length analysis and, in select cases, by Southern blotting (Akimoto et al., 2014) or using commercial PCR (Athena diagnostics). These studies received Institutional Review Board approval; all subjects provided written informed consent.

Differentiation and treatment of iNeurons for immunohistochemistry and Western blotting. Fibroblasts were maintained in Dulbecco's modified Eagle's medium (Lonza) supplemented with 10% heat-inactivated fetal bovine serum (Sigma-Aldrich), 100 units/ml penicillin, and 100 μg/ml streptomycin (Gibco) at 37° C., in an atmosphere containing 5% $CO_2$ and 95% air. Lentiviral shRNA against human PTBP1 (shPTB) cloned into pLKO.1 was a kind gift from Dr. Fu (University of California, San Diego). Both shPTB and non-silencing shRNA in the pLKO.1 vector (Sigma-Aldrich) were packaged in HEK293FT cells using Virapower (Invitrogen) packaging mix. Viral particles were collected 48 and 72 h after transfection.

To generate iNeurons, fibroblasts were seeded on a poly-D-lysine-coated surface and were transduced with pLKO.1 coding for shPTB1 or non-silencing control shRNA for 12-18 h in the presence of 5 μg/ml polybrene. Two days post-infection, cells were selected with 1.5 μg/ml puromycin for 48 h. At day 5, 10 ng/ml basic fibroblast growth factor (bFGF, GenScript) was added to the medium for two days. Cells were then maintained in DMEM/F12 medium containing 2% FBS, 25 mg/ml insulin (Sigma-Aldrich), 100 nM putrescine (Sigma-Aldrich), 50 mg/ml transferrin (Sigma-Aldrich), 30 nM sodium selenite (Sigma-Aldrich) and 15 ng/ml bFGF. After six days, the medium was enriched with B27 supplement (Gibco) and a cocktail of neurotrophic factors, including 10 ng/ml each of BDNF, GDNF (R&D Systems), NT3 (Peprotech), and CNTF (Sigma). Immunocytochemical analysis was performed 2-6 days later. For immunocytochemistry, cells were fixed with 4% paraformaldehyde, permeabilized with 0.5% Triton X-100/PBS and blocked in 5% skim milk/TBS-T. The following antibodies were used in 5% skim milk/TBS-T: mouse anti-MAP2 (Sigma, 1:2,000), mouse anti-Tuj 1 (Cell Signaling Technology, 1:2,000), mouse anti-Neurofilament H (Smi-32;

Millipore, 1:2,000), rabbit anti-Synapsin 1 (Syn1; Millipore, 1:500), rabbit anti-PSD95 (Abcam, 1:250), rabbit anti-Drebrin (Abcam, 1:500), goat anti-PTB1 (Abcam, 1:200 ICC, 1:1000 WB), rabbit anti-GP (1:1000) and rabbit anti-PR (1:1000). Secondary fluorescent antibodies (Invitrogen) were used at 1:1000 in 5% skim milk/TBS-T. Confocal microscopy was performed using Zeiss LSM 510 microscope.

For Western blot analysis, fibroblasts were transduced with shPTB1 or non-silencing control shRNA. Five days later, cell lysates were prepared and analysed by Western blot using an antibody to PTB1.

For treatment of iNeurons, fibroblasts were converted to iNeurons in 96-well plates and treated with compound 1a (2 or 4 μM) or DMSO for four days to analyze their effect on the accumulation of poly(GP) or poly(PR) protein inclusions. Serial pictures were generated using the BD Pathway Bioimager. For each condition, the percentage of cells containing poly(GP) or poly(PR) inclusions was calculated from 3-6 wells for each of 3 independent experiments.

RNA Fluorescent in situ hybridization (RNA-FISH) in fibroblasts and iNeurons. RNA FISH of fibroblasts and iNeurons treated with DMSO or compound 1a (2 μM) for four days was performed as previously described (Lagier-Tourenne et al., 2013) with some modifications. Briefly, plated cells were fixed in 4% PFA/DEPC-PBS, permeabilized with 0.2% Triton X-100/DEPC-PBS, washed twice with DEPC-PBS, dehydrated through 70% and 100% ethanol, and air dried. In some cases, iNeurons were treated with RNase A (2.5 μM; Qiagen) for 15 min at 37° C., or with DNase I (3 U/ml; Invitrogen) for 30 minutes at room temperature, prior to dehydration. Cells were incubated in hybridization buffer (10% dextran sulfate, 50% formamide, 50 mM sodium phosphate buffer (pH 7), 2×SSC) at 66° C. for 20-60 min. Prior to use, the locked nucleic acid probe (5'TYE563-CCCCGGCCCCGGCCCC-3' (SEQ ID NO:5), Batch #612968, Exiqon) was denatured at 80° C. for 75 s and diluted to 40 nM with hybridization buffer. Cells were hybridized with probe in a sealed, light-protected chamber for 16 h-24 h at 66° C. The coverslips were subsequently washed with 0.1% Tween-20/2×SSC for 5 min followed by three 10 min stringency washes in 0.1×SSC at 66° C. The cells were stained with Hoechst (Invitrogen), rinsed with DEPC-treated water, dehydrated through 70% and 100% ethanol and air dried. Coverslips were mounted with Prolong Gold antifade reagent (Life Technologies). RNA foci in iNeurons were visualized and quantified using a Zeiss Axiovert Fluorescence Microscope with apotome module. For each of 3 cell lines, 3 fields were randomly selected per condition. For each field, the number of foci-positive nuclei and the total number of nuclei were counted to determine the average percentage of foci-positive cells.

RNA extraction and quantitative PCR (qRT-PCR) of C9ORF72. iNeurons (three different cell lines, in triplicate) were harvested in lml of Trizol after treatment with DMSO or 1a (4 μM, 4 d). RNA was extracted using the Direct-Zol RNA kit combined with in-column DNase I digestion, as per the manufacturer's instructions (Zymo Research, Irvine, Calif., USA). RNA integrity was obtained using the Agilent 2100 Bioanalyzer (Agilent Technologies, Santa Clara, Calif., USA). cDNA was obtained after reverse transcription polymerase chain reactions (RT-PCR) using approximately 500 ng of RNA with random primers and the High Capacity cDNA Transcription Kit (Applied Biosystems, Foster City, Calif., USA) as per the manufacturer's instructions. Following standard protocols, qRT-PCR was conducted in triplicates for all samples using inventoried TaqMan gene expression assays for total C9ORF72 [transcript variants 1 (NM_145005.5), 2 (NM_018325.3), 3 (NM_001256054.1) (Hs00376619)], the long form of C9ORF72 [variants 2, 3 (Hs00945132)], and GAPDH (Hs00266705) (Applied Biosystems) on an ABI Prism 7900HT Fast Real-Time PCR System (Applied Biosystems). Relative quantification of C9ORF72 variants was determined using the ΔΔCt method and normalized to GAPDH.

SUPPLEMENTAL REFERENCES FOR EXAMPLES SECTION

Akimoto, C., Volk, A.E., van Blitterswijk, M., Van den Broeck, M., Leblond, C. S., Lumbroso, S., Camu, W., Neitzel, B., Onodera, O., van Rheenen, W., et al. (2014). A blinded international study on the reliability of genetic testing for GGGGCC-repeat expansions in C9orf72 reveals marked differences in results among 14 laboratories. J Med Genet 51, 419-424.

Almeida, S., Gascon, E., Tran, H., Chou, H. J., Gendron, T. F., Degroot, S., Tapper, A. R., Sellier, C., Charlet-Berguerand, N., Karydas, A., et al. (2013). Modeling key pathological features of frontotemporal dementia with C9ORF72 repeat expansion in iPSC-derived human neurons. Acta Neuropathol 126, 385-399.

Auron, P. E., Weber, L. D., and Rich, A. (1982). Comparison of transfer ribonucleic acid structures using cobra venom and S1 endonucleases. Biochemistry 21, 4700-4706.

Bellaousov, S., Reuter, J. S., Seetin, M. G., and Mathews, D. H. (2013). RNAstructure: web servers for RNA secondary structure prediction and analysis. Nucleic Acids Res 41, W471-474.

Bugaut, A., Murat, P., and Balasubramanian, S. (2012). An RNA hairpin to G-quadruplex conformational transition. J Am Chem Soc 134, 19953-19956.

Deane, F. M., Miller, C. M., Maguire, A. R., and McCarthy, F. O. (2011). Modifications to the Vilsmeier-Haack Formylation of 1,4-Dimethylcarbazole and Its Application to the Synthesis of Ellipticines. J Heterocyclic Chem 48, 814-823.

DeJesus-Hernandez, M., Mackenzie, I. R., Boeve, B. F., Boxer, A. L., Baker, M., Rutherford, N. J., Nicholson, A. M., Finch, N. A., Flynn, H., Adamson, J., et al. (2011). Expanded GGGGCC hexanucleotide repeat in noncoding region of C9ORF72 causes chromosome 9p-linked FTD and ALS. Neuron 72, 245-256.

Disney, M. D., Gryaznov, S. M., and Turner, D. H. (2000). Contributions of individual nucleotides to tertiary binding of substrate by a Pneumocystis carinii group I intron. Biochemistry 39, 14269-14278.

Ehresmann, C., Baudin, F., Mougel, M., Romby, P., Ebel, J. P., and Ehresmann, B. (1987). Probing the structure of RNAs in solution. Nucleic Acids Res 15, 9109-9128. Fojtik, P., Kejnovska, I., and Vorlickova, M. (2004). The guanine-rich fragile X chromosome repeats are reluctant to form tetraplexes. Nucleic Acids Res 32, 298-306.

Gendron, T. F., Bieniek, K. F., Zhang, Y. J., Jansen-West, K., Ash, P. E., Caulfield, T., Daughrity, L., Dunmore, J. H., Castanedes-Casey, M., Chew, J., et al. (2013). Antisense transcripts of the expanded C9ORF72 hexanucleotide repeat form nuclear RNA foci and undergo repeat-associated non-ATG translation in c9FTD/ALS. Acta Neuropathol 126, 829-844.

Hardin, C. C., Watson, T., Corregan, M., and Bailey, C. (1992). Cation-dependent transition between the quadruplex and Watson-Crick hairpin forms of d(CGCG3GCG). Biochemistry 31, 833-841.

Hingorani, D. V., Randtke, E. A., and Pagel, M. D. (2013). A CatalyCEST MRI Contrast Agent That Detects the Enzyme-Catalyzed Creation of a Covalent Bond. Journal of the American Chemical Society 135, 6396-6398.

Kumari, S., Bugaut, A., Huppert, J. L., and Balasubramanian, S. (2007). An RNA G-quadruplex in the 5' UTR of the NRAS proto-oncogene modulates translation. Nat Chem Biol 3, 218-221.

Lagier-Tourenne, C., Baughn, M., Rigo, F., Sun, S., Liu, P., Li, H. R., Jiang, J., Watt, A. T., Chun, S., Katz, M., et al. (2013). Targeted degradation of sense and antisense C9orf72 RNA foci as therapy for ALS and frontotemporal degeneration. Proc Natl Acad Sci USA 110, E4530-4539.

Marin, V. L., and Armitage, B. A. (2005). RNA guanine quadruplex invasion by complementary and homologous PNA probes. J Am Chem Soc 127, 8032-8033.

Mathews, D. H., Disney, M. D., Childs, J. L., Schroeder, S. J., Zuker, M., and Turner, D. H. (2004). Incorporating chemical modification constraints into a dynamic programming algorithm for prediction of RNA secondary structure. Proc Natl Acad Sci USA 101, 7287-7292.

Mergny, J. L., Phan, A. T., and Lacroix, L. (1998). Following G-quartet formation by UV-spectroscopy. FEBS Lett 435, 74-78.

Mullen, M. A., Olson, K. J., Dallaire, P., Major, F., Assmann, S. M., and Bevilacqua, P. C. (2010). RNA G-Quadruplexes in the model plant species *Arabidopsis thaliana:* prevalence and possible functional roles. Nucleic Acids Res 38, 8149-8163.

Peyret, N., Seneviratne, P. A., Allawi, H. T., and SantaLucia, J., Jr. (1999). Nearest-neighbor thermodynamics and NMR of DNA sequences with internal A.A, C.C, G.G, and T.T mismatches. Biochemistry 38, 3468-3477.

Plug, J. P. M., Koomen, G. J., and Pandit, U. K. (1992). An Expedient Synthesis Of 9-Hydroxyellipticine. Synthesis-Stuttgart, 1221-1222.

Puglisi, J. D., and Tinoco, I., Jr. (1989). Absorbance melting curves of RNA. Methods in enzymology 180, 304-325.

SantaLucia, J., Jr. (1998). A unified view of polymer, dumbbell, and oligonucleotide DNA nearest-neighbor thermodynamics. Proc Natl Acad Sci USA 95, 1460-1465.

Todd, A. K., and Neidle, S. (2011). Mapping the sequences of potential guanine quadruplex motifs. Nucleic Acids Res. 39, 4917-4927.

Todd, Peter K., Oh, Seok Y., Krans, A., He, F., Sellier, C., Frazer, M., Renoux, Abigail J., Chen, K.-c., Scaglione, K. M., Basrur, V., et al. (2013). CGG Repeat-Associated Translation Mediates Neurodegeneration in Fragile X Tremor Ataxia Syndrome. Neuron 78, 440-455.

Ziehler, W. A., and Engelke, D. R. (2001). Probing RNA structure with chemical reagents and enzymes. Curr Protoc Nucleic Acid Chem Chapter 6, Unit 6 1.

Zumwalt, M., Ludwig, A., Hagerman, P. J., and Dieckmann, T. (2007). Secondary structure and dynamics of the r(CGG) repeat in the mRNA of the fragile X mental retardation 1 (FMR1) gene. RNA biology 4, 93-100.

Documents Cited

Ash, P. E., Bieniek, K. F., Gendron, T. F., Caulfield, T., Lin, W. L., Dejesus-Hernandez, M., van Blitterswijk, M. M., Jansen-West, K., Paul, J. W., 3rd, Rademakers, R., et al. (2013). Unconventional translation of C9ORF72 GGGGCC expansion generates insoluble polypeptides specific to c9FTD/ALS. Neuron 77, 639-646.

Auron, P. E., Weber, L. D., and Rich, A. (1982). Comparison of transfer ribonucleic acid structures using cobra venom and S1 endonucleases. Biochemistry 21, 4700-4706.

Bugaut, A., Murat, P., and Balasubramanian, S. (2012). An RNA hairpin to G-quadruplex conformational transition. J Am Chem Soc 134, 19953-19956.

DeJesus-Hernandez, M., Mackenzie, I. R., Boeve, B. F., Boxer, A. L., Baker, M., Rutherford, N. J., Nicholson, A. M., Finch, N. A., Flynn, H., Adamson, J., et al. (2011). Expanded GGGGCC hexanucleotide repeat in noncoding region of C9ORF72 causes chromosome 9p-linked FTD and ALS. Neuron 72, 245-256.

Disney, M. D., Liu, B., Yang, W. Y., Sellier, C., Tran, T., Charlet-Berguerand, N., and Childs-Disney, J. L. (2012). A small molecule that targets r(CGG)(exp) and improves defects in fragile X-associated tremor ataxia syndrome. ACS Chem Biol 7, 1711-1718.

Donnelly, C. J., Zhang, P. W., Pham, J. T., Heusler, A. R., Mistry, N. A., Vidensky, S., Daley, E. L., Poth, E. M., Hoover, B., Fines, D. M., et al. (2013). RNA Toxicity from the ALS/FTD C9ORF72 Expansion Is Mitigated by Antisense Intervention. Neuron 80, 415-428.

Fratta, P., Mizielinska, S., Nicoll, A. J., Zloh, M., Fisher, E. M., Parkinson, G., and Isaacs, A. M. (2012). C9orf72 hexanucleotide repeat associated with amyotrophic lateral sclerosis and frontotemporal dementia forms RNA G-quadruplexes. Sci Rep 2, 1016.

Gendron, T. F., Belzil, V. V., Zhang, Y. J., and Petrucelli, L. (2014). Mechanisms of toxicity in C9FTLD/ALS. Acta Neuropathol 127, 359-376.

Gendron, T. F., Bieniek, K. F., Zhang, Y. J., Jansen-West, K., Ash, P. E., Caulfield, T., Daughrity, L., Dunmore, J. H., Castanedes-Casey, M., Chew, J., et al. (2013). Antisense transcripts of the expanded C9ORF72 hexanucleotide repeat form nuclear RNA foci and undergo repeat-associated non-ATG translation in c9FTD/ALS. Acta Neuropathol 126, 829-844.

Guan, L., and Disney, M. D. (2013). Covalent Small-Molecule-RNA Complex Formation Enables Cellular Profiling of Small-Molecule-RNA Interactions. Angewandte Chemie 52, 10010-10013.

Haeusler, A. R., Donnelly, C. J., Periz, G., Simko, E. A., Shaw, P. G., Kim, M. S., Maragakis, N. J., Troncoso, J. C., Pandey, A., Sattler, R., et al. (2014). C9orf72 nucleotide repeat structures initiate molecular cascades of disease. Nature.

Hardin, C. C., Watson, T., Corregan, M., and Bailey, C. (1992). Cation-dependent transition between the quadruplex and Watson-Crick hairpin forms of d(CGCG3GCG). Biochemistry 31, 833-841.

Lam, E. Y., Beraldi, D., Tannahill, D., and Balasubramanian, S. (2013). G-quadruplex structures are stable and detectable in human genomic DNA. Nat Commun 4:1796.

Mergny, J. L., Phan, A. T., and Lacroix, L. (1998). Following G-quartet formation by UV-spectroscopy. FEBS Lett 435, 74-78.

Mori, K., Arzberger, T., Grasser, F. A., Gijselinck, I., May, S., Rentzsch, K., Weng, S. M., Schludi, M. H., van der Zee, J., Cruts, M., et al. (2013a). Bidirectional transcripts of the expanded C9orf72 hexanucleotide repeat are translated into aggregating dipeptide repeat proteins. Acta Neuropathol 126, 881-893.

Mori, K., Weng, S. M., Arzberger, T., May, S., Rentzsch, K., Kremmer, E., Schmid, B., Kretzschmar, H. A., Cruts, M., Van Broeckhoven, C., et al. (2013b). The C9orf72 GGGGCC repeat is translated into aggregating dipeptide-repeat proteins in FTLD/ALS. Science 339, 1335-1338.

Reddy, K., Zamiri, B., Stanley, S. Y., Macgregor, R. B., Jr., and Pearson, C. E. (2013). The disease-associated r(GGGGCC)n repeat from the C9orf72 gene forms tract length-dependent uni- and multimolecular RNA G-quadruplex structures. J Biol Chem 288, 9860-9866.

Renton, A. E., Majounie, E., Waite, A., Simon-Sanchez, J., Rollinson, S., Gibbs, J.R., Schymick, J. C., Laaksovirta, H., van Swieten, J. C., Myllykangas, L., et al. (2011). A hexanucleotide repeat expansion in C9ORF72 is the cause of chromosome 9p21-linked ALS-FTD. Neuron 72, 257-268.

Sareen, D., O'Rourke, J. G., Meera, P., Muhammad, A. K., Grant, S., Simpkinson, M., Bell, S., Carmona, S., Ornelas, L., Sahabian, A., et al. (2013). Targeting RNA Foci in iPSC-Derived Motor Neurons from ALS Patients with a C9ORF72 Repeat Expansion. Sci Transl Med 5, 208ra149.

Velagapudi, S. P., Gallo, S. M., and Disney, M. D. (2014). Sequence-based design of bioactive small molecules that target precursor microRNAs. Nat Chem Biol 10, 291-297.

Wells, S. E., Hughes, J. M., Igel, A. H., and Ares, M., Jr. (2000). Use of dimethyl sulfate to probe RNA structure in vivo. Methods in enzymology 318, 479-493.

Xue, Y., Ouyang, K., Huang, J., Zhou, Y., Ouyang, H., Li, H., Wang, G., Wu, Q., Wei, C., Bi, Y., et al. (2013). Direct conversion of fibroblasts to neurons by reprogramming PTB-regulated microRNA circuits. Cell 152, 82-96.

Zamiri, B., Reddy, K., Macgregor, R. B., Jr., and Pearson, C. E. (2014). TMPyP4 Porphyrin Distorts RNA G-quadruplex Structures of the Disease-associated r(GGGGCC)n Repeat of the C9orf72 Gene and Blocks Interaction of RNA-binding Proteins. J Biol Chem 289, 4653-4659.

Ziehler, W. A., and Engelke, D. R. (2001). Probing RNA structure with chemical reagents and enzymes. Curr Protoc Nucleic Acid Chem Chapter 6, Unit 6 1.

Zu, T., Liu, Y., Banez-Coronel, M., Reid, T., Pletnikova, O., Lewis, J., Miller, T. M., Harms, M. B., Falchook, A. E., Subramony, S. H., et al. (2013). RAN proteins and RNA foci from antisense transcripts in C9ORF72 ALS and frontotemporal dementia. Proc Natl Acad Sci USA 110, E4968-4977.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of inhibiting repeat-associated non-ATG (RAN) translation and foci formation in cultured cells expressing r(GGGGCC)$_{66}$ and neurons trans-differentiated from fibroblasts of repeat expansion carriers, comprising contacting the cells with an effective amount of a compound of formula 3

3

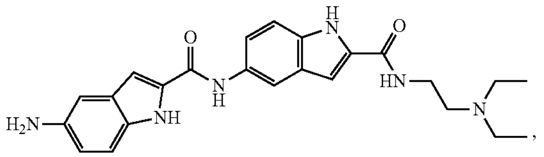

or a pharmaceutically acceptable salt thereof.

2. A method of treating a patient afflicted with ALS or FTD, comprising administering to the patient an effective dose of a compound of formula 3

3

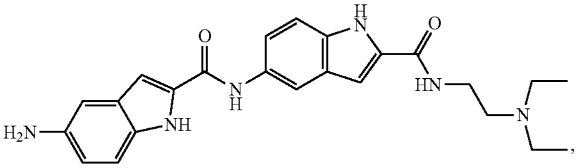

or a pharmaceutically acceptable salt thereof.

* * * * *